(12) United States Patent
Ni et al.

(10) Patent No.: US 10,667,499 B2
(45) Date of Patent: Jun. 2, 2020

(54) METHOD AND QUALITY CONTROL MOLECULAR BASED MOUSE EMBRYO ASSAY FOR USE WITH IN VITRO FERTILIZATION TECHNOLOGY

(71) Applicant: FUJIFILM Irvine Scientific, Inc., Santa Ana, CA (US)

(72) Inventors: Hsiao-Tzu Ni, Irvine, CA (US); Samira Es-Slami, Santa Ana, CA (US); Rebecca Susan Gilbert, Lake Forest, CA (US)

(73) Assignee: FUJIFILM Irvine Scientific, Inc., Santa Ana, CA (US)

( * ) Notice: Subject to any disclaimer, the term of this patent is extended or adjusted under 35 U.S.C. 154(b) by 0 days.

(21) Appl. No.: 14/249,208

(22) Filed: Apr. 9, 2014

(65) Prior Publication Data

US 2014/0302513 A1 Oct. 9, 2014

Related U.S. Application Data

(63) Continuation-in-part of application No. 14/214,314, filed on Mar. 14, 2014, now abandoned.

(60) Provisional application No. 61/783,557, filed on Mar. 14, 2013.

(51) Int. Cl.
*A01K 67/027* (2006.01)
(52) U.S. Cl.
CPC .... *A01K 67/0275* (2013.01); *A01K 2217/206* (2013.01); *A01K 2267/0393* (2013.01)
(58) Field of Classification Search
CPC .......... A01K 67/0275; A01K 2217/206; A01K 2267/0393; C12Q 1/68
See application file for complete search history.

(56) References Cited

U.S. PATENT DOCUMENTS

| | | |
|---|---|---|
| 2008/0175822 A1 | 7/2008 | Schatten et al. |
| 2009/0133134 A1 | 5/2009 | Wang |
| 2011/0044954 A1 | 2/2011 | Stice et al. |
| 2014/0302493 A1 | 10/2014 | Ni et al. |

FOREIGN PATENT DOCUMENTS

| | | |
|---|---|---|
| EP | 1 847 595 A1 | 10/2007 |
| WO | WO-2011/025736 A1 | 3/2011 |

OTHER PUBLICATIONS

Keiser et al., Cloning,3(1): 23-30, 2001.*
Ramirez et al., Biol. of Reproduction, 80: 1216-1222, 2009.*
Yu et al., Biol. of Reproduction, 67: 282-286, 2002.*
Punt-van der Zalm, RBM Online, 18(4): 529-535, 2009.*
Zhang et al., Reproductive Toxicity, 19: 473-478.*
Taft, Theriogenology, 69(1): 10-16, 2008.*
VerMilyea et al., P-410, Steril, 94(4)(Suppl), p. S212, 2010.*
PCT International Search Report and Written Opinion dated Jul. 15, 2015 in related PCT Patent Application No. PCT/US15/25007 20 pages.
Baczkowski et al., "Methods of Embryo Scoring in Vitro Fertilization," Reproductive Biology, (2004), 4(1):5-22.
Bavister, B.D., "Culture of preimplantation embryos: facts and artifacts," Hum Reprod Update, (Mar. 1995);1(2):91-148.
Es-Slami et al. (Oct. 2013). "Evaluation of continuous single culture via the expression of OCT-4 SOX-2 and CDX-2 in mouse embryos." Poster session presented at the meeting of the American Society for Reproductive Medicine, Boston, MA.
Gada et al., "Potential of inner cell mass outgrowth and amino acid turnover as markers of quality in the in vitro fertilization laboratory," Fertility and Sterility, (2012), 98(4):863-869.
Gardner et al., "Quality control in human in vitro fertilization," Semin Reprod Med. (Nov. 2005);23(4):319-24.
Gerrity, M., "Mouse Embryo Culture Bioassay", In Vitro Fertilization and Embryo Transfer: A Manual of Basic Techniques, Don P. Wolf, Editor, 1988, pp. 57-75.
Jones et al., "Novel strategy with potential to identify developmentally competent IVF blastocysts," Human Reproductions, (2008), 23(8):1748-1759
Lane, M., "Mechanisms for managing cellular and homeostatic stress in vitro," Theriogenology (Jan. 1, 2001);55(1):225-36.
Leese, H.J., "Metabolism of the preimplantation mammalian embryo," Oxf Rev Reprod Biol., (1991), 13:35-72.
PCT International Search Report and Written Opinion dated Aug. 11, 2014 in related PCT Patent Application No. PCT/US2014/029410.
Plachta et al., "Oct4 kinetics predict cell lineage patterning in the early mammalian embryo," Nature Cell Biology, (2011), 13(2):117-123.
"QC Toxicity Testing" accessed from http://ww.embryotech.com/qc/mea.thm on Dec. 10, 2015, p. 1, published Mar. 25, 2008.
Boiani et al., "Oct4 distribution and level in mouse clones: consequences for pluripotency", Genes & Development, 2002, 16:1209-1219.
Piliszek et al., "Ex Utero Culture and Live Imaging of Mouse Embryos", Methods Mol Biol., 2011, 770:243-257.
Caperton et al., Assisted Reproductive Technologies do not Alter Mutation Frequency or Spectrum, PNAS, Mar. 20, 2007, vol. 104, No. 12, pp. 5085-5090.
Li et al., Comparative Analysis of Development-Related Gene Expression in Mouse Preimplantation Embryos With Different Developmental Potential, Molecular Reproduction and Development, 2005, 72:152-160.

(Continued)

*Primary Examiner* — Thaian N. Ton
(74) *Attorney, Agent, or Firm* — Foley & Lardner LLP

(57) ABSTRACT

A method for qualitatively assessing products used in in vitro fertilization is provided. Also disclosed is an improved quality control assay for use in clinical Assisted Reproductive Technologies (ART).

19 Claims, 15 Drawing Sheets
(15 of 15 Drawing Sheet(s) Filed in Color)

(56) References Cited

OTHER PUBLICATIONS

McDole et al., Generation and Live Imaging of an Endogenous Cdx2 Reporter Mouse Line, Genesis. Oct. 2012; 50(10): 775-782.
Brafman et al., "Long-term human pluripotent stem cell self-renewal on synthetic polymer surfaces", Biomaterials, 2010, 31:9135-9144.
Taft, "Virtues and limitations of the preimplantation mouse embroyo as a model system", Theriogenology,2008, pp. 10-16.
Vermilyea, "Redefining the Mouse Embryo Assay (MEA): Novel Time-Lapse Imagery and Continuous Surveillance VS. 'Snap Shot' Observation", 2010, P-410, Steril, 94(4)(Suppl).
Moskaluk et al., "Cdx2 Protein Expression in Normal and Malignant Human Tissues: An Immunohistochemical Survey Using Tissue Microarrays", Modern Pathology, Augusta 16.9, Sep. 2003, pp. 913-919.
Werling et al., "CDX2, a Highly Sensitive and Specific Marker of Adenocarcinomas of Intestinal Origin: An Immunohistochemical Survey of 476 Primary and Metastatic Carcinomas", American Journal of Surgical Pathology, Mar. 2003, vol. 27, Issue 3, pp. 303-310.

\* cited by examiner

Figure 1
Oct-4 study in optimal and sub-optimal growth conditions
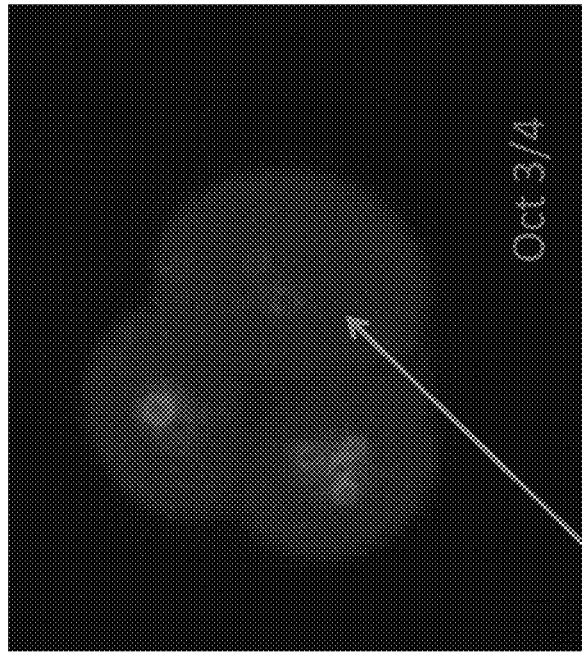
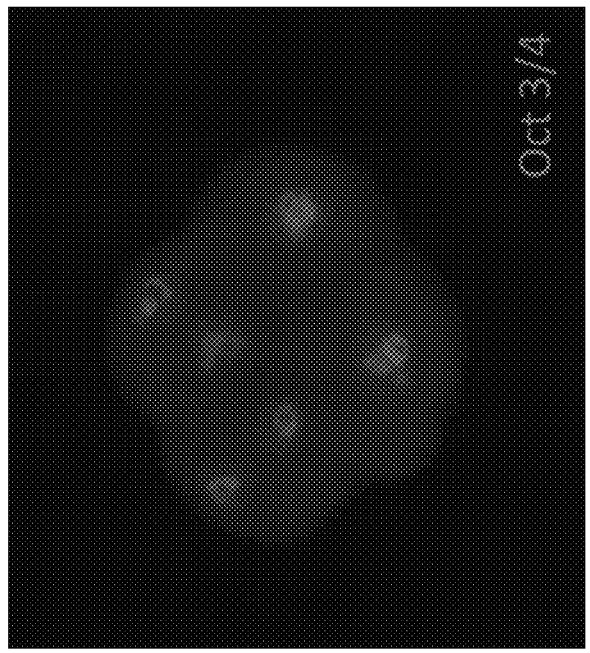
Optimal growth conditions
Sub-optimal growth conditions
Note: lack of Oct 3/4 staining on the right cell of the embryo (slow embryo)

Oct-4 study in optimal and sub-optimal growth conditions

Optimal growth conditions

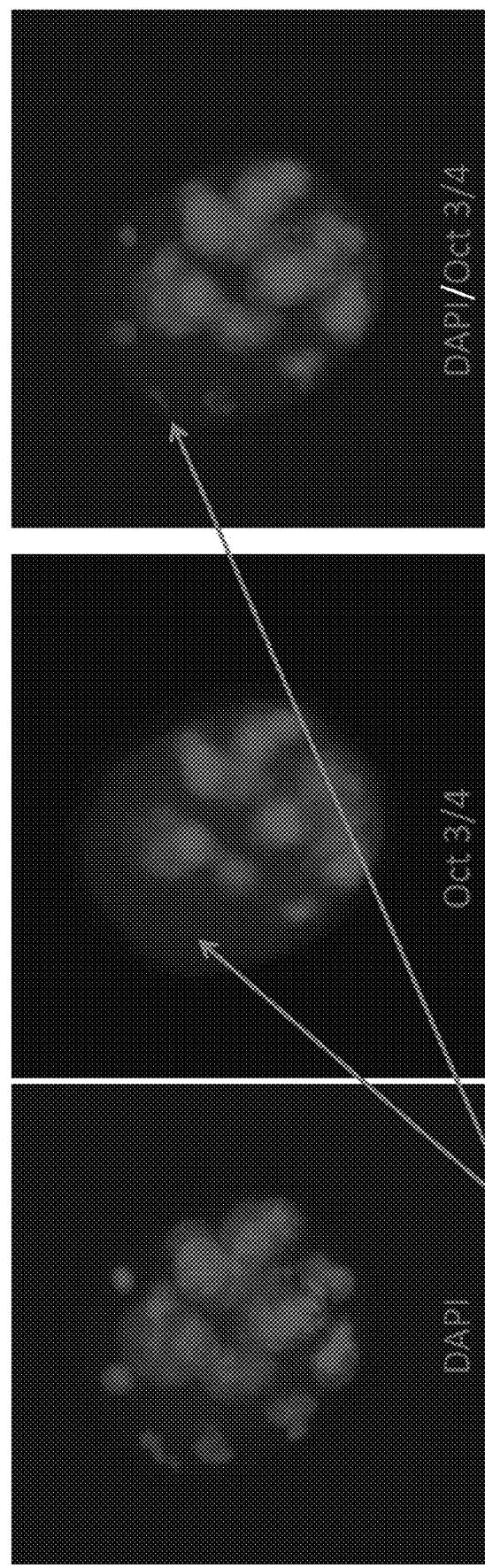

Sox-2 study in optimal and sub-optimal growth conditions

Sub-optimal growth conditions

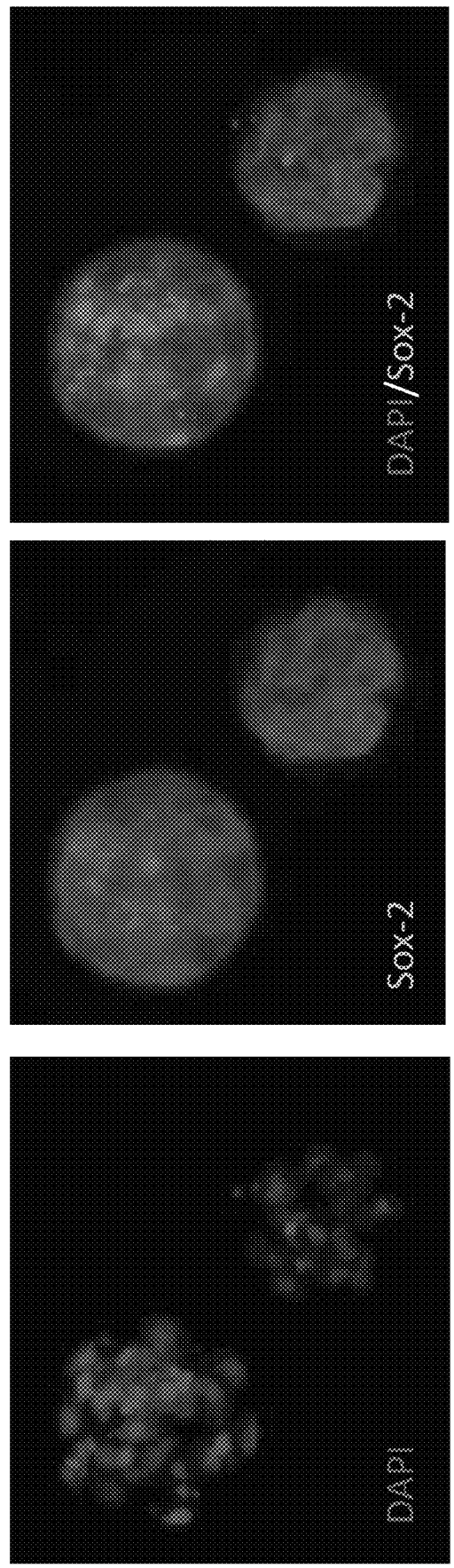

Figure 5
Oct4-GFP mouse embryos after 48 hr culture
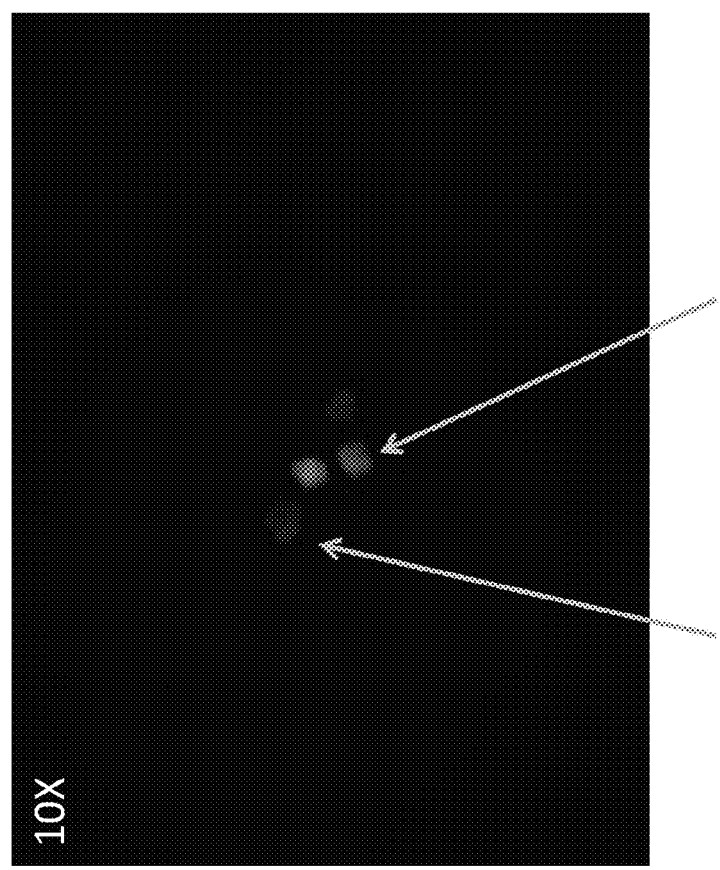
Figure 5B
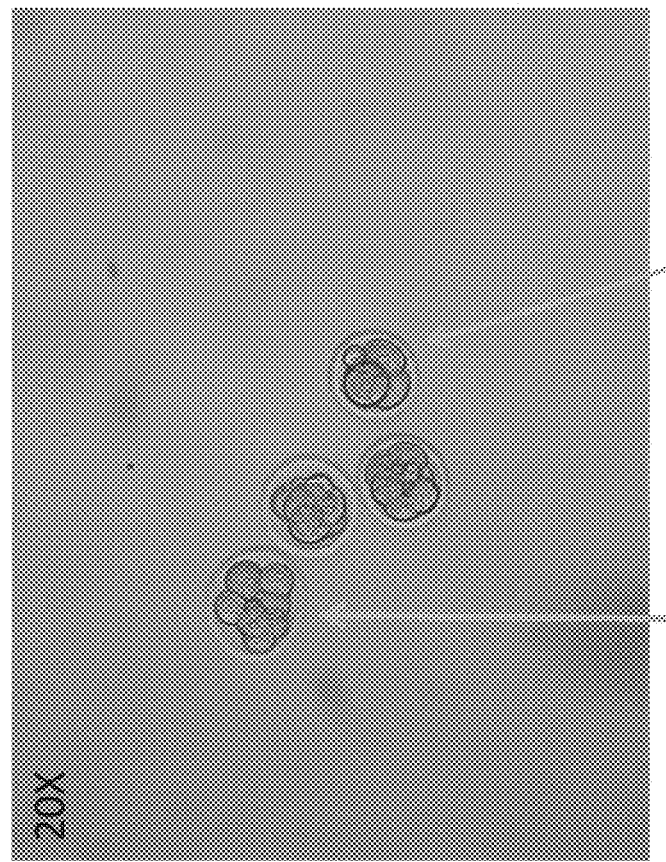
Figure 5A

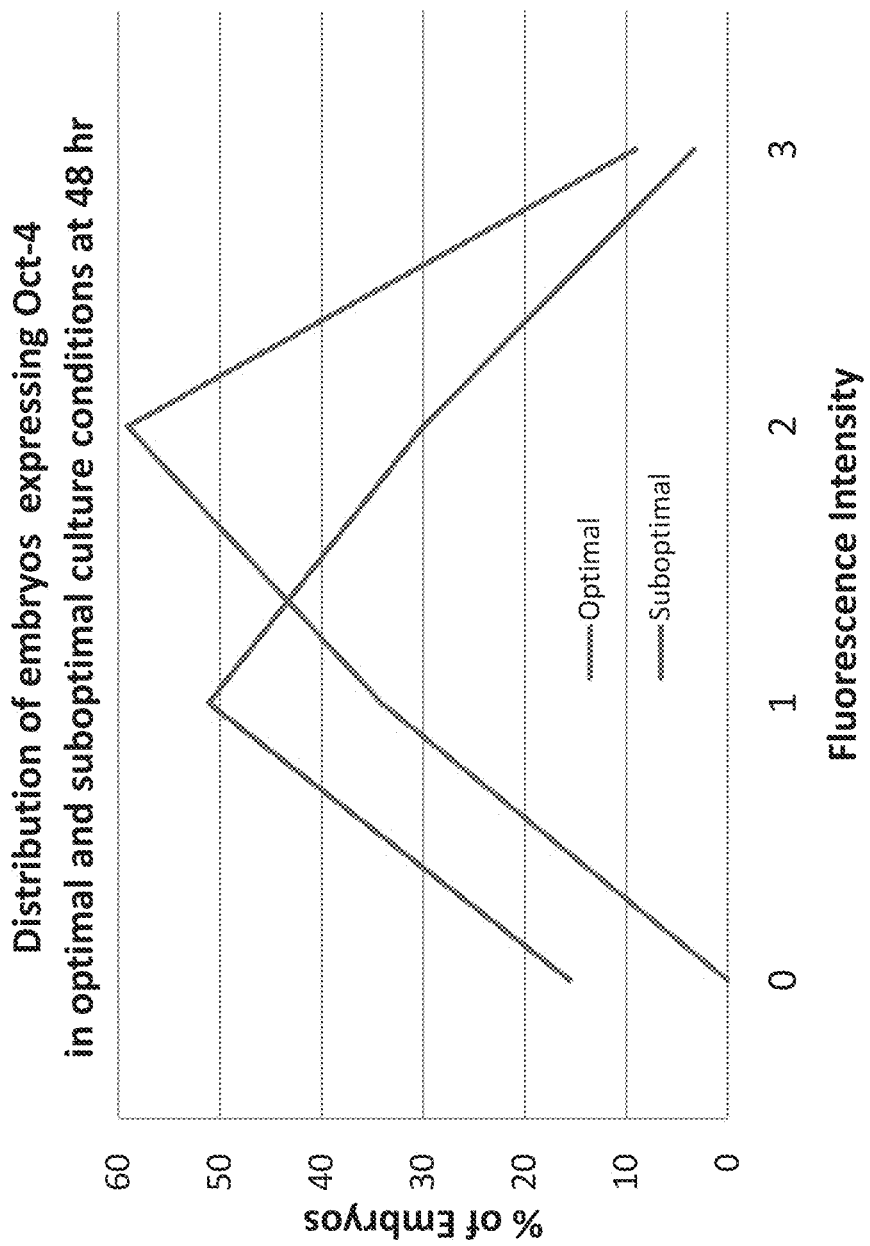

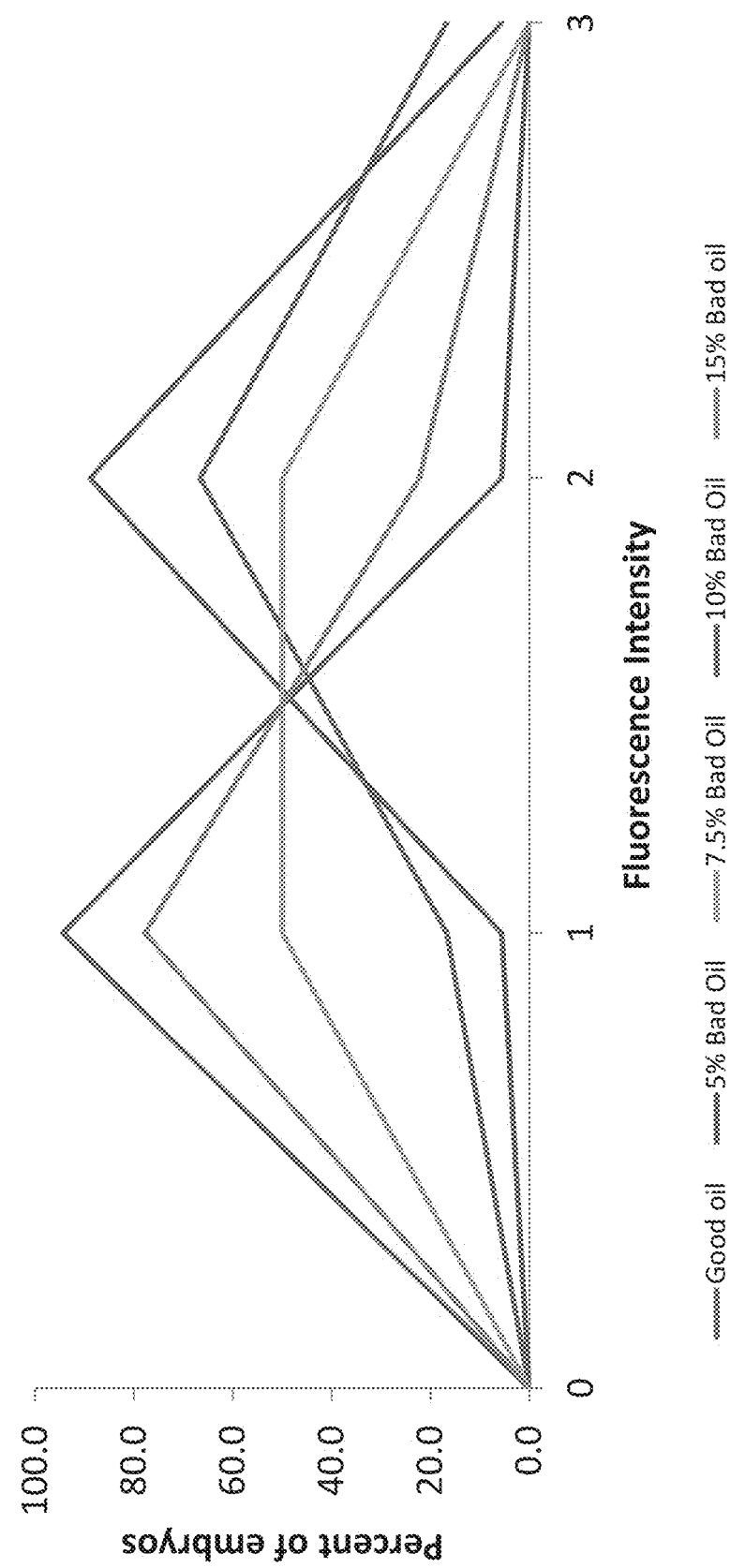

METHOD AND QUALITY CONTROL MOLECULAR BASED MOUSE EMBRYO ASSAY FOR USE WITH IN VITRO FERTILIZATION TECHNOLOGY

CROSS-REFERENCE TO RELATED PATENT APPLICATIONS

This application is a Continuation-in-Part of U.S. application Ser. No. 14/214,314, filed Mar. 14, 2014, which claims priority from U.S. Provisional Application Ser. No. 61/783,557, filed Mar. 14, 2013, entitled A METHOD AND QUALITY CONTROL MOLECULAR BASED MOUSE EMBRYO ASSAY FOR USE WITH IN VITRO FERTILIZATION TECHNOLOGY, which is incorporated herein by reference in its entirety.

BACKGROUND OF THE INVENTION

Field of the Invention

The present invention relates to a method for assessing products used in cellular biology, for example, in vitro fertilization. Also disclosed is a quality control assay for use in clinical Assisted Reproductive Technologies (ART).

Description of the Related Art

The in vitro fertilization (IVF) laboratory plays a fundamental role in the treatment of infertile couples. Ensuring proper Quality Control (QC) in the IVF laboratory is critical to the success of any IVF program, as the environment of the laboratory can alter the quality of the embryos produced. An optimal culture medium and a stable environment are necessary for the successful development of human embryos in vitro. The ultimate role of the embryology laboratory is to maintain the inherent viability of the gametes and embryos in an environment outside the female reproductive tract. The dynamic nature of pre-implantation embryo development is unique because, unlike somatic cell culture, embryos are constantly and rapidly changing, both in morphology and function (Leese 1991; Bavister 1995).

During development, pre-implantation embryos change rapidly, in just a matter of days, from a metabolically quiescent, undifferentiated single cell under the genetic control of maternal transcripts into a dynamic, multi-celled embryo that has developed homeostatic mechanisms and its own functioning genome (Leese 1991; Lane 2001; Gardner et al. 2005). The early embryo, which depends on a pyruvate-based metabolism and is solely dependent on mitochondrial oxidative phosphorylation for energy production; like a unicellular organism, the early embryo lacks many key regulatory functions for pH and osmotic control. After compaction at the eight- to 16-cell stage (dependent on species), there is a change in metabolic control to a highly glycolytic metabolism. Concomitantly, there is also a marked transition in the functional complexity of other cellular mechanisms as the embryo's physiology becomes more like that of a somatic cell. It is the initially crude nature of homeostatic regulation in the early embryo and its subsequent development through later stages of pre-implantation development that pose significant challenges in the laboratory. Maintenance of a favorable in vitro environment is essential for maximizing viability and promoting ongoing development.

Perturbations to the environment surrounding the embryo during development in culture, relative to "normal" conditions encountered in the reproductive tract, result in reduced embryo viability and impaired development. As discussed below, there is a need for objective, sensitive, and reproducible methods and assays for testing materials used in human IVF for embryo toxicity as well as growth promoting and inhibiting factors.

SUMMARY OF THE INVENTION

It is often difficult to assess the impact of suboptimal environment using morphology as a marker on embryos and other cells. For example, in certain instances, embryos that develop to apparently morphologically normal blastocysts may, in fact, not be completely normal or healthy. Such apparently morphologically normal blastocysts can be compromised at the cellular level, for example. Compromised blastocysts may have a reduced capacity to implant and produce a successful term pregnancy. The environment that an embryo is exposed to during collection and culture can significantly alter its developmental potential and cellular regulation. The mouse embryo assay (MEA) has been the gold standard to examine the applicability of culture media and environment without involving human materials. The basic techniques and protocols employed for performing the MEA are set forth in *In Vitro Fertilization and Embryo Transfer: A Manual of Basic Techniques* (Don P. Wolf, Editor), 1988, pages 57-75; the contents of which are hereby incorporated by reference in their entirety. Briefly, the assay involves superovulation of female mice with pregnant mare serum gonadotropin (PMSG) and human chorionic gonadotropin (hCG). The mice are placed with males at the time of hCG injection and killed 24 hours following hCG to obtain one-cell embryos or 36 hours after injection to obtain two-cell embryos. One-cell embryos are selected for use if they have two polar bodies visible; two cell embryos are selected for use if they look morphologically normal.

The MEA is used for toxicity and functionality testing of reproductive media, labware, or any device coming into contact with gametes and/or embryos. The rationale for requiring information on this test as a special control for class II assisted reproduction devices is that it is a good surrogate indicator of potential toxicity of materials used in assisted reproduction devices to gametes and/or embryos. The FDA has recognized that the MEA is currently the most appropriate test for embryo toxicity. Briefly, both one-cell and two-cell assays are used, and these are identical except that one-cell embryos are flushed from the mouse oviduct earlier than two-cell embryos. Whether a one-cell or two-cell MEA is used, the bioassay should represent, as closely as possible, the corresponding procedures used for which the device is used for human IVF, such as the acquisition, maintenance, culture, transfer (relocation) and cryopreservation of embryos. Typically, embryo morphology is assessed and blastocyst formation is determined after 96 hours of culture. If more than 80% of the zygotes have reached the blastocyst stage, the medium, labware, or other equipment tested are considered suitable for clinical use.

In addition to detecting embryo toxicity, the MEA is capable of detecting suboptimal raw materials, media, and contact materials associated with IVF and ART. However, there are a number of limitations of this assay which are often overlooked. For example, the assay can only detect conditions which are grossly and harshly embryo toxic. The MEA cannot detect or differentiate growth promoting or inhibiting factors at a very early stage in development.

Embodiments described herein generally are directed to systems and methods for providing a molecular based mouse embryo assay (mMEA) for use as a quality control in, for example, in vitro fertilization (IVF) arenas and/or Assisted Reproductive Technologies (ART), and more specifically to an improved assay for assessing embryonic development from the one-cell or two-cell stage to the blastocyst stage.

From this description, in conjunction with other items, the advantages of the invention will become clear and apparent based upon the hereinafter descriptions and claims, which are supported by drawings as described in the following sections.

In one aspect, a quality control method for assessing products used for human IVF or ART is provided. The method includes providing a transgenic embryo (at least one-cell) and culturing the embryo in vitro for a specified period of time. The method further includes evaluating the embryonic development from one-cell or two-cell to the blastocyst stage and beyond. Acceptability or failure of the tested items is determined based upon qualitative and quantitative analyses of the embryo development. Optionally, the one-cell embryo includes at least one fluorescent protein transgene operably linked to the regulatory region of at least one embryonic development/pluripotency regulator.

The transgene may include a reporter gene encoding a selected fluorescent protein such as green fluorescent protein (GFP), red fluorescent protein, cyan fluorescent protein, orange fluorescent protein or yellow fluorescent protein.

In another aspect, the quality control method and assay are designed to evaluate test items used in IVF environments and/or ART. The test items may include gamete and embryo culture media, gamete and embryo handling/processing media (to include washing and separation media), transport media, enzymes for denuding oocytes, gradient for sperm separation, freezing/vitrification media, thawing/warming media, pipette and embryo handling devices, lab-ware used in the process of human in vitro fertilization including but not limited to Petri dishes, centrifuge tubes, cryopreservation and Cryo-storage devices, and any solutions, reagents or devices involved with in vitro ART related procedures.

In another aspect, evaluation of embryonic development is accomplished by analysis of general embryo morphology related to the developmental stages of the embryos and/or the location/quantity/quality of fluorescence. Preferably, the embryo is derived from a mammal and can include murine, porcine, equine, bovine, ovine, leporine, and non-human primate embryo.

In still another aspect, the operably linked embryonic pluripotency regulator may include without limitation Oct-4, Sox2, Nanog, CDX2 and Rex1 as well as their upstream mediators and downstream effectors that play a role in ensuring normal embryo development.

Embryo development may be assessed at any or all stages including 1 and 2-cell-stages, 4-cell stage, 8-cell stage, morula stage, blastocyst stage and gastrulation stage.

A quality control assay or kit for use in clinical ART to evaluate products used in the process of handling and preserving human gametes and producing, culturing and preserving human embryos is likewise provided. The assay advantageously includes a transgenic one-cell embryo harvested from a transgenic mammal, wherein the embryo comprises at least one reporter gene operably linked to the regulatory region of at least one embryonic pluripotency marker; and instructions for evaluating ART products and IVF culture conditions. The instructions can include incubating a transgenic one-cell embryo under certain culture conditions and evaluating embryo development based upon morphology from the one and two-cell to blastulation and gastrulation stages.

Optionally, the reporter gene encodes a fluorescent protein, such as Green Fluorescent Protein, Red Fluorescent Protein, Cyan Fluorescent Protein, Orange Fluorescent Protein, or Yellow Fluorescent Protein.

In another aspect, the assay includes at least one transgenic embryo, wherein the transgene comprises at least one embryonic pluripotency regulator and/or its regulatory regions (e.g., upstream mediators and/or downstream effectors), where the pluripotency regulator plays a role in ensuring normal embryo development. The test items/growth conditions may be evaluated based on embryo growth, development and quality based upon assessment of embryo morphology and/or qualitative/quantitative assessment of fluorescence. The acceptable threshold for optimal embryo growth and development is based on individual set criteria depending on test items and expected development under normal/control conditions. In the event that the test items do not meet the established acceptance criteria compared to a normal control, they would be considered suboptimal or embryotoxic (i.e., unacceptable).

In still another aspect of the invention, an embryo assay with enhanced sensitivity for use in quality control of clinical human ART/IVF is described. The assay may include a transgenic one-cell embryo. The embryo can include at least one reporter gene operably linked to at least one gene associated with embryonic development. Preferably, the embryo expresses a transgenic/reporter gene differentially under optimal and sub-optimal culture conditions. In another aspect, the culture conditions are embryotoxic. Also provided is a test item such as, for example, embryo culture media, gamete handling media, enzymes for denuding oocytes, gradient for sperm separation, freezing media, thawing media, pipettes and embryo handling devices, or labware used in the process of human in vitro fertilization including but not limited to Petri dishes, centrifuge tubes, cryopreservation and cryostorage devices.

The invention disclosed herein further includes a method for enhancing the sensitivity of an embryo assay using analysis of embryo development to the blastocyst stage. The method includes providing a transgenic embryo comprising at least one reporter gene operably linked to the regulatory region of at least one embryonic pluripotency marker; incubating the transgenic embryo under culture conditions that utilize the test item(s); and evaluating embryo development morphologically and/or via the expression of said embryonic marker from one-cell to blastocyst and/or gastrulation stages.

Optionally, the method for enhancing the sensitivity of an embryo assay further includes evaluating expression of the embryonic marker at the blastocyst stage and beyond (gastrulation). The evaluation may comprise determining fluorescence of the reporter gene. The assay may detect embryotoxicity in culture media and/or culture materials. In one aspect, the assay detects functionality of media and suitability of materials used in clinical in vitro fertilization environments.

A modified, transgenic embryo, comprising at least one transgene operably linked to the regulatory region of at least one embryonic pluripotency regulator is disclosed. The embryonic pluripotency regulators include these regulators' genes as well as their upstream mediators and downstream effectors that play a role in ensuring normal embryo development. Advantageously, the transgene is a reporter gene. The reporter gene may be a fluorescent or luminescent protein such as green fluorescent protein, red fluorescent protein, cyan fluorescent protein, orange fluorescent protein, or yellow fluorescent protein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a color photograph of mouse embryos incubated from the 2-cell to blastocyst stage under optimal and suboptimal IVF growth conditions. After 48 hours in culture, the mouse embryos were stained with an anti-OCT-3/4 antibody and visualized by fluorescence microscopy.

FIGS. 2A and 2B represent the expression of OCT-4 under optimal or suboptimal growth conditions. FIG. 2A is a color photograph of a mouse embryo incubated under optimal growth conditions. FIG. 2B is a color photograph of a mouse embryo incubated under sub-optimal growth conditions. Embryos were grown to the blastocyst stage, then stained with DAPI (blue; nuclear stain) and anti-OCT-3/4 antibody (red). The embryo was visualized by fluorescence microscopy.

FIGS. 3A-3C represent the expression of SOX2 under optimal or suboptimal growth conditions. FIG. 3A is a color photograph of a mouse embryo incubated under optimal growth conditions. FIG. 3B is a color photograph of a mouse embryo incubated under suboptimal growth conditions. FIG. 3C is a color photograph of mouse embryos incubated under suboptimal growth conditions. Embryos were grown to the blastocyst stage, stained with DAPI (blue) and anti-SOX2 antibody (green), then photographed under fluorescence microscopy.

FIG. 5A shows Oct4-GFP transgenic mouse embryos cultured for 48 hours based on morphological analysis using light microscopy. FIG. 5B shows 4-GFP transgenic mouse embryos cultured for 48 hours based on morphological analysis using fluorescence microscopy. Embryos expressing enhanced green fluorescent protein (EGFP) under the control of the Oct-4 promoter demonstrate low (FI 0-1) and high (FI 2-3) levels of fluorescence intensity.

FIG. 6A indicates the percentage of embryos that had not (blue) or had (red) reached the 8-cell stage by 48 hours, as determined by light microscopy. FIG. 6B indicates the percentage of embryos with low (blue) or high (red) fluorescence at 48 hours. FIG. 6C indicates the percentage of transgenic mouse embryos in each blastocyst stage (degenerated or early blastocyst, blue; blastocyst, red; expanded, green; hatching, purple) based on morphological analysis using light microscopy. FIG. 6D indicates the percentage of embryos in each blastocyst stage based on morphological analysis under fluorescence microscopy. FIG. 6E indicates the percentage of embryos exhibiting each level of fluorescence (no fluorescence, blue; low intensity fluorescence, red; medium intensity fluorescence, green; high intensity fluorescence, purple) at 48 hours that developed to the indicated stage by 96 hours.

FIG. 7 indicates the distribution of embryos grown under suboptimal (red) or optimal (blue) conditions according to the fluorescence intensity as determined at 48 hours.

FIGS. 8A-8E graphically depict an embryo development study where transgenic mouse embryos containing CDX2-GFP were used in a molecular-based mouse embryo assay (mMEA) in the presence of different qualities of oil: (1) good oil, (2) 5% bad oil, (3) 7.5% bad oil, (4) 10% bad oil, and (5) 15% bad oil. FIG. 8A graphically illustrates the percentage of embryos that had not (blue) or had (red) developed to the 8-cell stage by 48 hours, as determined by light microscopy evaluation of visual morphology. FIG. 8B graphically illustrates the percentage of embryos at 48 hours for each of the categories of oil using molecular expression analysis via low (blue) or high (red) fluorescence intensity. FIG. 8C graphically illustrates the percentage of development at 96 hours for each of the categories of oil using a visual morphological evaluation. FIG. 8D graphically illustrates the percentage of embryos at 96 hours rated as a low fluorescence intensity (FI 0-1, blue) or a high fluorescence intensity (FI 2-3, red) for each of the categories of oil using molecular expression analysis. FIG. 8E depicts the distribution of embryos in optimal and suboptimal culture conditions according to their fluorescence status.

DETAILED DESCRIPTION OF THE PREFERRED EMBODIMENTS

Figure 2A:
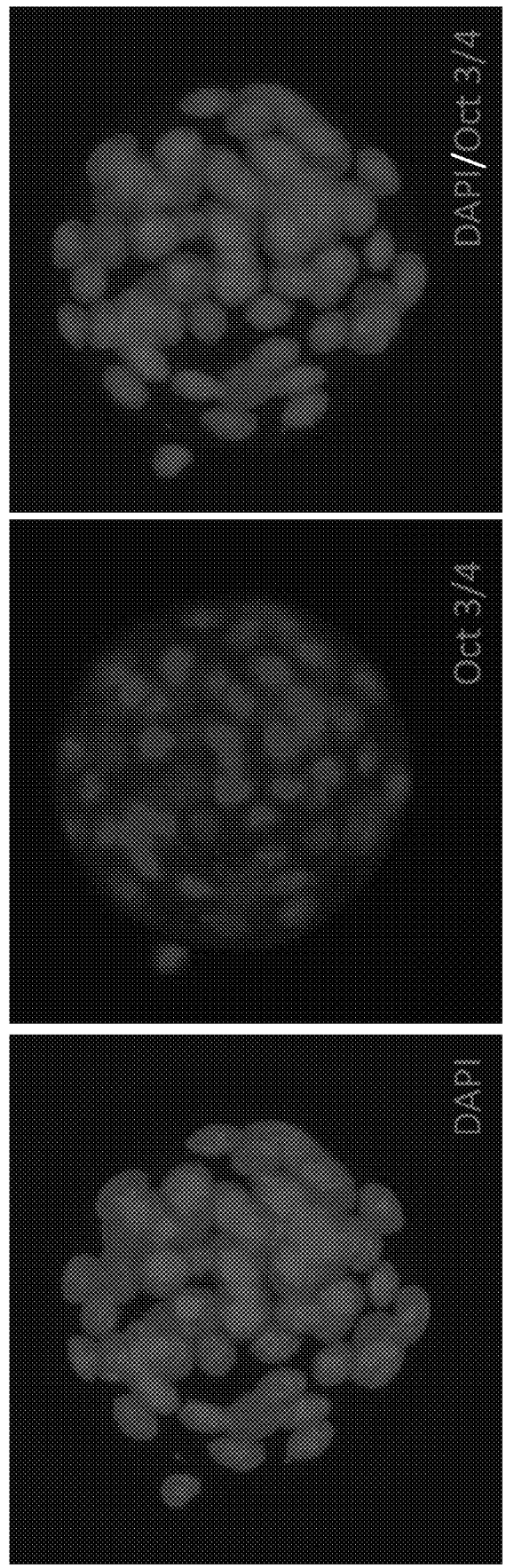

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of"

shall mean excluding more than trace amount of other ingredients and substantial method steps recited. Embodiments defined by each of these transition terms are within the scope of this invention.

As used herein, the term "regulatory region" includes all of the elements and/or sequences of the gene of interest that are required for proper expression of that gene. Known regulatory elements include promoters, enhancers, silencers, insulators, and the like. Regulatory regions can include regions upstream of the transcription start site (5' untranslated region), downstream of the transcription start site, within introns, in the 3' untranslated region, or within coding sequences. For example, the regulatory region may include only the minimum essential elements of the viability marker gene to direct expression of the transgene. In other aspects, the regulatory region may include larger portions or substantially all of the viability marker gene, including part or all of the coding region. The regulatory may also include upstream mediators and/or downstream effectors.

As used herein, the term "viability marker" refers to any gene whose expression or lack thereof indicates the viability of the embryo during at least one stage of development. Viability markers include embryonic development markers and pluripotency markers. Generally, these markers include embryonic stem cell associated transcript genes. Pluripotent stem cell markers, as used herein, are expressed at a predictable level and location at a predictable time of embryonic development. Viability markers may be expressed at a certain stage of embryo development. Expression at a certain time during development may indicate that the embryo is developing normally; lack of expression may indicate abnormal development. Alternatively, viability markers may be genes that are not normally expressed at a certain stage of embryo development, and whose expression at such a time indicates abnormal development.

As used herein, the term "reporter gene" includes any gene that can be operably linked to the regulatory region of a viability marker and can be visualized or otherwise evaluated to determine its expression. In a preferred embodiment, the reporter gene is a fluorescent or luminescent protein. In some embodiments, the reporter gene may be or include, for example, an epitope tag (e.g., HIS, FLAG, HA) that is recognized by an antibody.

As used herein, "acceptability" of a product is determined by rates of survival, development, and/or reporter gene expression of blastocysts that are approximately equal to or better than that observed in the control or a standard (e.g., greater than 80% developed blastocysts). Likewise, "failure" as used herein is determined by rates that are below that observed in the control or a standard.

As used herein, "control conditions" are the conditions known to provide for optimal embryo growth and/or development. "Test conditions" are conditions employing the IVF product to be tested for its effect on embryo growth and development.

"Optimal" conditions as used herein, refers to conditions which promote healthy, unfettered embryonic development. "Sub-optimal" conditions, by contrast, are culture conditions which allow for some cellular growth but the growth is slower and less robust than what would be predicted to be observed under optimal culture conditions. "Embryo toxicity" as used herein, refers to culture conditions which induce abnormal development or embryo death.

"Assisted Reproductive Technology" or ART, as used herein, includes all fertility treatments in which both female gametes (eggs or oocytes) and male gametes (sperm) are handled. In Vitro Fertilization (IVF) is one of several assisted reproductive techniques used to assist infertile couples in conceiving a child. IVF refers to the procedure by which eggs are removed from the female's ovary and fertilized with sperm in a laboratory procedure. The fertilized egg (embryo) can be cryopreserved for future use or transferred to the uterus.

As used herein, "blastocyst" refers to a structure in early embryonic development consisting of a ball of cells with surrounding wall (trophectoderm or TE) which will form the placenta, a fluid filled cavity (blastocoels) which will form the amniotic sac, and an internal cluster of cells called the inner cell mass (ICM) from which the fetus arises. Other terms relating to the invention are defined and described in more detail below.

Generally disclosed herein are methods, systems and kits related to assessing the impact on the culture and development of biological cells of certain culture conditions or parameters. For example, some embodiments relate to a quality control method for assessing the culture conditions for in vitro fertilization or ART. For example, fertilized embryos harvested from reporter-transgenic animal, such as a mouse, are used to detect possible detrimental or suboptimal culture conditions or parameters. Effectively, the transgenic embryos provide a more sensitive and functionally relevant qualitative quality control (QC) assay for testing and qualifying devices for use in clinical in vitro fertilization and ART laboratories, for example.

As will be described in greater detail below, the method can include providing a transgenic blastocyst with at least one-cell; culturing the blastocyst under in vitro or Assisted Reproductive Technology ("ART") culture conditions, and evaluating blastocyst differentiation to determine the acceptability of the culture conditions. Quality control assays and methods of performing quality control assays as described in detail below include a mammalian transgenic embryo (at least one-cell). In preferred embodiments, the embryo is at the one- or two-cell stage. The mammalian embryo can be obtained from bovine, ovine, porcine, murine, canine, equine, simian, or human origin. In some embodiments, the mammalian embryo is porcine, equine, or bovine. More commonly, the embryo is murine derived.

The molecular MEA as described herein can have many advantages over the standard MEA that is currently used to test IVF reagents and consumables. The standard MEA is based on a determination of the morphology of the embryos at one or more stages of development. In contrast, the molecular MEA can utilize molecular analysis of developmental markers to determine the effects of a test product on embryo development. Also, the molecular MEA can couple molecular analysis of developmental markers with morphological analysis to determine the effects of a test product on embryo development. Benefits include availability of early results, increased sensitivity, and the availability of automation. Suboptimal culture conditions may be apparent as early as 48 hours when using mouse embryos. In addition, IVF reagents having small deleterious effects, especially effects that affect gene expression but not morphology, may be observed. Reporter gene expression, as represented, for example, by fluorescence, can be determined quantitatively or qualitatively, including for example, by a mechanized method, allowing for increased automation (e.g., an automated assessment).

Titles or subtitles may be used in the specification for the convenience of a reader, which are not intended to influence the scope of the present invention. Additionally, some terms used in this specification are more specifically defined below.

I. Methods

The culture of gametes and embryos is an integral part of any reproductive research laboratory, as is the use of plastic and glassware, and other consumables, such as gloves, plates, media, chemicals, and oil. In the IVF setting, the quality control of all consumable and materials is important for maintaining an optimal environment for embryo culture, thus ensuring normal embryo physiology and subsequent pregnancy rates. Thus, some embodiments relate to methods of evaluating the impact or effect on an embryo (e.g., potential toxicity) of IVF consumables and materials.

As used herein, IVF consumables include, without limitation, media, media supplements, plastic ware, tubing, pipettes, pipette tips, etc. or any material that comes into contact with human eggs or embryos. Plastic and glassware can include assisted reproduction needles, laboratory gloves, assisted reproduction catheters, and assisted reproduction microtools such as pipettes or other devices used in the laboratory to denude, micromanipulate, hold, or transfer embryos. IVF consumables further include assisted reproduction labware, including without limitation, syringes, IVF tissue culture dishes, IVF tissue culture plates, pipette tips, dishes, plates, and other vessels that come into physical contact with gametes, embryos, or tissue culture media. As used herein, IVF consumables can include assisted reproduction water and water purification systems intended to generate high quality sterile, pyrogen-free water for reconstitution of media used for aspiration, incubation, transfer or storage of embryos for IVF or other assisted reproduction procedures as well as for use as the final rinse for labware or other assisted reproduction devices which will contact the embryos. Non-limiting examples of products that may be tested can be found in 21 C.F.R. 884.6100, et seq., which is incorporated herein by reference in relevant part.

In one aspect, this invention relates to a method for assessing a product used for Assisted Reproductive Technologies (ART), the method may include, for example, providing a transgenic embryo comprising at least one cell, wherein the embryo comprises at least one transgene operably linked to the regulatory region of at least one embryonic viability marker; culturing the embryo in vitro for a specified duration; evaluating expression of the transgene during at least one stage of development of the embryo; and determining the acceptability or failure of the product based upon said evaluation, wherein the product is used in the method in a manner similar to its intended use in ART. In some embodiments, the transgene is a reporter gene.

In one aspect, this invention relates to a method for assessing a product used for Assisted Reproductive Technologies (ART). The method may include, for example, providing a transgenic embryo, wherein the embryo comprises at least one reporter gene operably linked to the regulatory region of at least one embryonic viability marker; culturing the embryo in vitro for a specified duration; evaluating expression of the at least one reporter gene during at least one stage of development of the embryo; and determining the acceptability or failure of the product based upon said evaluation, wherein the product is used in the method in a manner similar to its intended use in ART.

In one aspect, the invention relates to methods for assessing a product used for Assisted Reproductive Technologies (ART). The method can include, for example, providing a transgenic embryo, wherein the embryo comprises at least one reporter gene operably linked to the regulatory region of at least one embryonic viability marker; utilizing a product that is proposed for use in ART; culturing the embryo in vitro for a specified duration; evaluating expression of the at least one reporter gene in the cultured embryo for at least a part of the specified duration; and assessing the impact on the embryo of utilizing the product based upon expression of the at least one reporter gene. In some embodiments, the product is used in the method in a manner similar to its intended use in ART. In some embodiments, the method further comprises determining the acceptability or failure of said product based upon the assessment.

In some embodiments, the methods can include, for example, evaluating the morphology of the embryo during at least one stage of development of the embryo. In some embodiments, the transgenic embryo is provided as a one-cell embryo or two-cell embryo. In some embodiments, the transgenic embryo is from a mammal. In some embodiments, the mammal is murine, porcine, equine, bovine, ovine, leporine or non-human primate. In some embodiments, the transgenic embryo is from a rat. In a preferred embodiment, the transgenic embryo is from a mouse. In some embodiments, the transgene or at least one reporter gene encodes a fluorescent protein. In some embodiments, the evaluating step comprises determining the fluorescence intensity of the fluorescent protein.

The specified duration can depend on a number of factors, including the species of embryo used, the expression pattern of the transgene(s) of interest, the intended use of the test product, etc. In some embodiments, the specified duration is one, two, three, four, five, six, seven, eight, nine, ten, or more days. Some examples of non-limiting duration time points are 24, 48, 72 and 96 hours. The duration can also be such that one or more evaluations are done on one or more days (e.g., once, twice, three, four, five, six, seven, eight, nine or ten different times during one or more 24 hour periods over a 1-10 day period for example). In some embodiments, the specified duration is determined by the desired developmental stage, for example through the 2-cell-stage, 4-cell stage, 8-cell stage, morula stage, blastocyst stage, gastrulation stage, or beyond.

In some embodiments, the evaluating step can include, for example, one or more of: i. capturing at least one image of said embryo; ii. determining a level of expression of said reporter gene based on the image; and iii. comparing said level of expression to a threshold level and/or a control level. In some embodiments, steps ii and iii are performed by a computer. In some embodiments, the evaluating may include measuring light emission and/or intensity visually, or using a device for the same.

In some embodiments, the evaluating step further may include comparing the expression of the transgene or at least one reporter gene in a transgenic embryo that has been cultured under control conditions.

In some embodiments, the at least one stage of development can be, for example, the 1-cell stage, 2-cell-stage, 4-cell stage, 8-cell stage, morula stage, blastocyst stage, and/or gastrulation stage.

In some embodiments, the product can be deemed acceptable, for example, if expression of the transgene or at least one reporter gene is sufficient to indicate that the embryo is not affected by the use of the test product. In some embodiments, sufficiency of expression is determined by comparison to a control and/or comparison to other cells being tested. In some embodiments, sufficiency of expression is determined by comparison to a pre-determined standard. In some embodiments, the product is deemed acceptable if the morphology of the embryo is appropriate. In some embodiments, appropriate morphology is determined by comparison to a control. In some embodiments, appropriate morphology is determined by comparison to a pre-determined standard. In some embodiments morphology and expression can be assessed to determine the impact of a parameter on embryo development. For example, if both morphology and expression are positive, then an assessment of no negative impact or a positive impact can be made. If the morphology is favorable, but expression is poor at one or more time points, then an appropriate assessment can be made, for example, that there is an adverse or negative impact.

In some embodiments, the level of fluorescence of embryos in a test condition is compared to the level of fluorescence of embryos in a control condition to determine whether the test condition is acceptable. In some embodiments, the percentage of embryos exhibiting a certain level of fluorescence (e.g., 0-1 or 2-3) is compared. In some embodiments, an acceptable level of fluorescence observed in embryos in test condition is 50% or greater of fluorescence observed in embryos in control condition. In some embodiments, an acceptable level of fluorescence observed in embryos in test condition is 60% or greater of fluorescence observed in embryos in control condition. In some embodiments, an acceptable level of fluorescence observed in embryos in test condition is 70% or greater of fluorescence observed in embryos in control condition. In some embodiments, an acceptable level of fluorescence observed in embryos in test condition is 80% or greater of fluorescence observed in embryos in control condition. In some embodiments, an acceptable level of fluorescence observed in embryos in test condition is 90% or greater of fluorescence observed in embryos in control condition. In some embodiments, an acceptable level of fluorescence observed in embryos in test condition is 100% or greater of fluorescence observed in embryos in control condition. It should be understood that any subvalue or subrange from within the values described above are contemplated for use with the embodiments described herein.

In some embodiments, the location of fluorescence of embryos in a test condition is compared to the location of fluorescence of embryos in a control condition to determine whether the test condition is acceptable. In some embodiments, the percentage of embryos exhibiting a certain level of fluorescence (e.g., FI 0-1 or FI 2-3) in a certain location (e.g., nucleus or cytoplasm) is compared. In some embodiments, an acceptable level of fluorescence observed in the given location of embryos in test condition is 50% or greater of fluorescence observed in the given location of embryos in control condition. In some embodiments, an acceptable level of fluorescence observed in the given location of embryos in test condition is 60% or greater of fluorescence observed in the given location of embryos in control condition. In some embodiments, an acceptable level of fluorescence observed in the given location of embryos in test condition is 70% or greater of fluorescence observed in the given location of embryos in control condition. In some embodiments, an acceptable level of fluorescence observed in the given location of embryos in test condition is 80% or greater of fluorescence observed in the given location of embryos in control condition. In some embodiments, an acceptable level of fluorescence observed in the given location of embryos in test condition is 90% or greater of fluorescence observed in the given location of embryos in control condition. In some embodiments, an acceptable level of fluorescence observed in the given location of embryos in test condition is 100% or greater of fluorescence observed in the given location of embryos in control condition. It should be understood that any subvalue or subrange from within the values described above are contemplated for use with the embodiments described herein.

In some embodiments, the marker or transgene present in the embryo is a gene that would be expected to be turned off at a specific time on embryo development, for example at the time the embryo is examined. In some embodiments, an acceptable level of fluorescence observed in embryos in test condition is 80% or less of fluorescence observed in embryos in control condition. In some embodiments, an acceptable level of fluorescence observed in embryos in test condition is 70% or less of fluorescence observed in embryos in control condition. In some embodiments, an acceptable level of fluorescence observed in embryos in test condition is 60% or less of fluorescence observed in embryos in control condition. In some embodiments, an acceptable level of fluorescence observed in embryos in test condition is 50% or less of fluorescence observed in embryos in control condition. In some embodiments, an acceptable level of fluorescence observed in embryos in test condition is 40% or less of fluorescence observed in embryos in control condition. In some embodiments, an acceptable level of fluorescence observed in embryos in test condition is 30% or less of fluorescence observed in embryos in control condition. In some embodiments, an acceptable level of fluorescence observed in embryos in test condition is 20% or less of fluorescence observed in embryos in control condition. In some embodiments, an acceptable level of fluorescence observed in embryos in test condition is 10% or less of fluorescence observed in embryos in control condition. It should be understood that any subvalue or subrange from within the values described above are contemplated for use with the embodiments described herein.

In some embodiments, at least 50% of control embryos must exhibit fluorescence at a specified level (e.g., FI 0-1 or FI 2-3) in order to indicate the assay was successful. In some embodiments, at least 60%, 70%, 80%, 90% or 100% of control embryos must exhibit fluorescence at the specified level (e.g., FI 0-1 or FI 2-3) in order to indicate the assay was successful. It should be understood that any subvalue or subrange from within the values described above are contemplated for use with the embodiments described herein.

In some embodiments, the level of fluorescence of embryos in a test condition is compared to a standard. In some embodiments, the standard is based on the transgene/marker used, the species embryo used, the type of reagent being tested, the microscope used, or any other parameter. In some embodiments, the standard requires that at least 50% of the embryos in the test condition exhibit fluorescence at a specified level (e.g., FI 0-1 or FI 2-3). In some embodiments, the standard requires that at least 60% of the embryos in the test condition exhibit fluorescence at a specified level. In some embodiments, the standard requires that at least 70% of the embryos in the test condition exhibit fluorescence at a specified level. In some embodiments, the standard requires that at least 80% of the embryos in the test condition exhibit fluorescence at a specified level. In some embodiments, the standard requires that at least 90% of the embryos in the test condition exhibit fluorescence at a specified level. In some embodiments, the standard requires that at least 100% of the embryos in the test condition exhibit fluorescence at a specified level. It should be understood that any subvalue or subrange from within the values described above are contemplated for use with the embodiments described herein.

In some embodiments, the product can be, for example, one or more of needles, catheters, microtools, labware, syringes, tissue culture dishes, tissue culture plates, pipette tips, dishes, plates, water, water purification systems, media, media supplements, and other vessels, devices, or reagents that come into physical contact with gametes, embryos or tissue culture media. In some embodiments, the product can be, for example, one or more of gamete and embryo culture media, gamete and embryo handling/processing media, transport media, enzymes for denuding oocytes, gradient for sperm separation, freezing/vitrification media, thawing/warming media, pipette and embryo handling devices, labware used in the process of human ART including but not limited to Petri dishes, centrifuge tubes, cryopreservation and cryo-storage devices, and any solutions, reagents or devices involved with ART.

In some embodiments, the viability marker can be any marker or gene associated with the development and/or health of a blastocyst or embryo. Also, for example, the marker or gene can be any gene, gene family associated with, or gene regulated by one or more of Oct-4, Cdx2, Sox2, and Nanog. In some embodiments, the fluorescent protein is a green fluorescent protein, a red fluorescent protein, a yellow fluorescent protein, an orange fluorescent protein, a cyan fluorescent protein, or the like.

Some embodiments relate to methods for enhancing the sensitivity of an embryo assay using embryo development to the blastocyst stage. The methods can include for example providing a transgenic embryo comprising at least one reporter gene operably linked to at least one embryonic pluripotency marker, incubating the transgenic embryo under culture conditions utilizing test items and/or control; and evaluating embryo development morphologically and via the expression of the embryonic marker from one-cell to blastocyst and gastrulation stages. The methods can further include evaluating expression of the embryonic marker at the blastocyst stage and beyond (gastrulation). Evaluation of expression can be measured, for example, by determining fluorescence or other light emission of the reporter gene. The embryo assay can detect embryo-toxicity in culture media and/or culture materials. In another embodiment, the assay can detect functionality of media and suitability of materials used in clinical in vitro fertilization environments.

An assay for testing the effectiveness of glassware washing techniques, cleansing of surgical instruments (aspiration needle), transfer catheters and any other item that comes in contact with the human eggs, sperm or embryos is likewise encompassed by the current technology and methods.

II. Transgenic Embryos

The term "transgenic" means of or pertaining to a segment of DNA that has been incorporated into a host genome or is capable of replication in a host cell and is capable of causing expression of one or more cellular products. Exemplary transgenes can provide the host cell, or animals developed therefrom, with a novel phenotype relative to the corresponding non-transformed cell or animal. "Transgenic animal" means a non-human animal, usually a mammal, having a non-endogenous nucleic acid sequence present as an extrachromosomal element in at least a portion of its cells or stably integrated into its germ line DNA.

Transgenesis is used to create transgenic mammals such as mice with reporter genes linked to a gene of interest. Methods in molecular genetics and genetic engineering are described generally in the current editions of Molecular Cloning: A Laboratory Manual, (Sambrook et al.); Oligonucleotide Synthesis (M. J. Gait, ed.); Animal Cell Culture (R. I. Freshney, ed.); Gene Transfer Vectors for Mammalian Cells (Miller & Calos, eds.); Current Protocols in Molecular Biology and Short Protocols in Molecular Biology, 3.sup.rd Edition (F. M. Ausubel et al., eds.); and Recombinant DNA Methodology (R. Wu ed., Academic Press). Thus, transgenic technology is well established. See, e.g. Transgenic Mouse: Methods and Protocols (M. Hofker and J. Deursen, Eds.) in Methods in Molecular Biology (Vol. 209) (the contents of which are hereby incorporated by reference in their entirety).

In one aspect, the transgenic mammal includes a reporter gene linked to the regulatory region of a viability marker gene of interest. Reporter genes include, for example, fluorescent or luminescent proteins such as luciferase, green fluorescent protein, or red fluorescent protein. Fluorescent proteins can include, without limitation, blue/UV proteins such as TagBFP, mTagBFP2, azurite, EBFP2, mKalama1, Sirius, sapphire, and T-sapphire. Fluorescent proteins can also include cyan proteins such as ECFP, cerulean, SCFP3A, mTurquoise, mTurquoise2, monomeric Midoriishi-Cyan, TagCFP, and mTFP1. In a preferred embodiment, the fluorescent protein is a green protein such as EGFP, Emerald, Superfolder GFP, Monomeric Azami Green, TagGFP2, mUKG, mWasabi, or Clover. Yellow fluorescent proteins including EYFP, Citrine, Venus, SYFP2, ZsYellow1, and TagYFP are likewise contemplated for use as a reporter gene. Orange proteins for use as reporter genes can include Monomeric Kusabira-Orange, $mKO_k$, mKO2, mOrange, and mOrange2. Red proteins such as HcRed1, mRaspberry, mCherry, mStrawberry, mTangerine, tdTomato, TagRFP, mApple, mRuby, and mRuby2. Far-red proteins include, without limitation, mPlum, HcRed-Tandem, mKate2, mNeptune, and NirFP. The embryos of transgenic mice express the reporter protein(s) at the same time and location that e the marker(s) of interest is expressed.

In some embodiments, the transgenic animal comprises more than one transgene operably linked to the regulatory region of an embryonic viability marker. In some embodiments, the transgenic animal comprises 2, 3, 4, or more transgenes operably linked to the regulatory region of different embryonic viability marker. For example, a transgenic animal may comprise multiple fluorescent reporter genes, each linked to a different viability marker such that multiple fluorescent proteins are expressed in the embryo. The expression of the reporter genes may change as the embryo develops. In a preferred embodiment, all of the reporter genes that are expressed in the embryo can be analyzed by the same method, e.g., fluorescence microscopy. Without being bound by theory, it is believed that analysis of multiple genes in the same embryo(s) can lead to increased sensitivity.

In some aspects, gametes will be harvested from male and female animals (sperm and oocytes, respectively) and the oocytes will be fertilized in vitro using methods similar to IVF protocols. In some aspects, the male and female animals will be mated, and resulting embryo(s) harvested from the female animal at the desired time point. In a preferred embodiment, the female is wild type (i.e., does not carry the transgene) and the male is transgenic. Without being bound by theory, it is believed that expression of the transgene from maternal transcripts in an early embryo will result in undesirable background expression of the transgene. In some embodiments, the female is transgenic and the male is wild type. In some embodiments, both the male and the female comprise the transgene. In some embodiments, the female and male animals carry one or more different transgenes. One of skill in the art would understand that different viability markers are expressed at different times during development, and as such expression from maternal transcripts is not an important consideration for all viability markers.

As used herein, viability markers include embryonic development markers and pluripotency markers, as well as gene families and/or genes regulated by such markers. Generally, these markers include embryonic stem cell associated transcript genes. Pluripotent stem cell markers, as used herein, are expressed at a predictable level and location at a predictable time of embryonic development. Pluripotent stem cell (PS)-specific markers include, but are not limited to, the family of octamer transcription factors, i.e. Oct-4; genes regulated by Oct-4; the family of Sox genes, e.g., Sox 1, Sox2, Sox3, Sox 15, and Sox 18; the family of Klf genes such as Klf4 and Klf5; the family of Nanog genes, e.g., NANOG, as well as their regulatory regions. Other viability markers include, without limitation, the TGF-beta superfamily and their receptors, i.e. Activ RIB/ALK-4, GDF-3 and Lefty, the cryptic protein family, i.e. Cripto-1, the integrin family, i.e. integrin alpha 6 (CD49f) and integrin beta 1 (CD29), the Podocalyxin family, i.e. PODX-1, the FGF family, i.e. FGF4 and FGF-5, the Forkhead box transcription factor family, i.e. FoxD3, the T-box family of transcription factor, i.e. TBX3 and TBX5, the family of developmental pluripotency associated molecules, i.e. Dppa2, Dppa3/Stella, Dppa4 and Dppa5/ESG1, the LRR family, i.e. 5T4, the cadherin family, i.e. E-Cadherin, the connexin family of transmembrane proteins, i.e. Connexin-43 and Connexin-45, the F-box family of "other" category, i.e. FBOXO15, the family of chemokine/chemokine receptors i.e. CCR4 and CXCR4, the ATP-binding Casstet Transporters, i.e. ABCG2. Additional common known markers involved in OCT-4 and/or SOX2-mediated stemness maintenance are Utf1, TERT, Zscan4, CD9, CD15/Lewis X, CD25, CD30/TNFRSF8, CD90/Thy1, Alkaline Phosphatase/ALPL, alpha HCG, HCG, DNMT3B, GBX2, GCNF/NR6A1, Gi24/Dies1/VISTA, LIN-28A, LIN-28B, LIN-41, c-Myc, Rex-1/ZFP42, sFRP-2, Smad2, Smad2/3, SPARC, STAT3, SUZ12, TOBX2, TEX19/19.1, THAP11, and TROP-2. A person of skill in the art would understand that any viability marker, currently known or to be discovered, is encompassed by the present invention.

Also contemplated and disclosed is a modified, transgenic embryo, comprising at least one transgene operably linked to at least one embryonic pluripotency marker. The embryonic pluripotency markers and their upstream mediators and downstream effectors play a role in ensuring normal embryo development. In a preferred embodiment, the transgene is a reporter gene. In a preferred embodiment, the reporter gene is a fluorescent or luminescent protein selected from the group consisting of green fluorescent protein, red fluorescent protein, cyan fluorescent protein, orange fluorescent protein, yellow fluorescent protein.

III. Analysis of Embryo Development

The suitability of a particular product for use in clinical ART is evaluated based on embryo growth, development and/or quality. Qualitative scoring of embryo development can be based upon a qualitative/quantitative assessment of expression of a marker, for example, by assessing light emission or intensity or fluorescence, or any other visual indicator such as color. In some embodiments, assessment of embryo morphology also can be done and utilized together with the expression analysis.

In some embodiments, one or more controls can be included for comparative purposes. For both control and test products, roughly the same number of one-cell or two-cell embryos can be cultured in vitro. For example, in one non-limiting approach 30 embryos can be divided up between ten drops that are each cultured in a separate well. In some aspects, the control and test products can each have approximately 30 embryos divided up between ten drops and wells. Any other suitable number can be tested and run as well.

Qualitative analysis of embryo development can be accomplished by analyzing the developing embryo by measuring or assessing color, light intensity or fluorescence visually, for example, via light microscopy which may include UV light to visualize fluorescent protein expression. Such measuring or assessing also can include or can take into account the location of the color, light or fluorescence within the blastocyst. As will be seen in greater detail with reference to the Examples and Figures, optimal and suboptimal culture conditions can be assessed or determined based upon location of the fluorescence (nuclear versus cytoplasmic localization, etc.), as well as the intensity of fluorescence.

As will be readily appreciated by a skilled artisan, the acceptable threshold for optimal embryo growth can be based on individual set criteria, for example culture conditions, the developmental marker, the transgene/reporter gene, and test items. Blastocyst differentiation can be evaluated via confocal microscopy. In a preferred embodiment, acceptability of culture conditions is based upon the qualitative analysis of embryo development via fluorescence microscopy. In a particularly preferred embodiment, embryonic development is observed via an embryo scope (e.g., EmbryoScope® Time-lapse system, Unisense Fertilitech A/S), wherein a picture of developing embryos can be taken as desired, for example, approximately every 10 minutes and a time-lapse video can be generated to track all stages of embryo development. As illustrated in the Figures (as will be described in greater detail with reference to the Examples), embryo development can be determined both in terms of chronology (stage reached for a specific culture duration) and embryo quality, both morphologically and functionally, by assessing the location and quantity/intensity of the fluorescence or other light or indicator. Expression of single markers in a test cell will provide evidence of undifferentiated or differentiated phenotype, according to the expression pattern. Expression of genes that are down-regulated and/or lack of expression of genes that are up-regulated upon development/differentiation may indicate the stage of development of the embryo.

Embryo development and quality can be assessed qualitatively and/or quantitatively. In some embodiments, qualitative assessment of fluorescence (and morphology) is performed, for example by visualization of the blastocyst under a microscope. A qualitative analysis of expression (e.g., via fluorescence) may involve, for example, a subjective rating of fluorescence intensity of the test samples, and optionally control samples (e.g., no fluorescence, low intensity, medium intensity, high intensity). In one non-limiting embodiment, a scale of 0-3 can be used where a rating of 0-1 means little or no light or expression, 2-3 means medium to high expression or light. The rating can be done, for example, based upon relative expression of a group of samples to each other. For example, a relative rating of 5, 10, 20, or 30 wells, where each well is categorized on a scale. In some embodiments, the scale is between 0 and 3. In some aspects, a score of 2 or greater can mean that the development is normal. In some aspects, a score of 2 or greater, coupled with proper development in an MEA can mean that the development is normal or acceptable. Conversely, a score of 0-1 can mean that the tested product or parameter is unacceptable, even where the visual morphology if assessed (e.g., using MEA looks acceptable). Such a low score can help avoid false positives that otherwise would have occurred if one were using MEA alone. Acceptable limits may be determined, for example, as described above.

In a preferred embodiment, embryo development can be assessed quantitatively or semi-quantitatively. Non-limiting examples include assessment of fluorescence or light intensity by a computer attached to the microscope, assessment of intensity based on a photograph of the embryo, measurement of light intensity using a photometer or a fluorometer, or any other method of determining fluorescence intensity. In some embodiments, determination of fluorescence intensity is automated. In some embodiments, a camera or other device present on the microscope detects the fluorescence signal(s) and transmits the signal to a software program capable of determining fluorescence intensity and/or comparing fluorescence intensity to intensity from other embryos, e.g., embryos grown under control conditions.

In some embodiments, the fluorescence intensity and/or location of the fluorescence for each embryo grown under each condition (e.g., test and control) is measured separately. In some embodiments, multiple embryos are grown in a confined area, for example a single droplet of media, and the fluorescence intensity of all of the embryos in the area are assessed or measured together. As noted above, the assessment or qualitative/quantitative measure can be based upon a comparative assessment to other tested samples, including a control, if present.

As noted, the methods can include, if desired, qualitative assessment based upon visually assessing morphology, for example, as done with the mouse embryo assay (MEA). Such assessment can include a comparison of embryonic development from day 0, starting at the 1-cell stage, to the blastocyst stage, for example, by 96 hours in culture. One day after fertilization, for example, one would expect to observe cleavage of the embryo in both the control and embryos cultured on the test product. Two days after fertilization, in the case of murine assays, one would expect to observe eight-cell stage of development under optimal conditions in both the control and test product if the test product is to be deemed acceptable for use in ART. The number of embryos that develop to the blastocyst stage is likewise quantified in both the control and test product. An assessment is made with regard to suitability of the test product for use in ART based upon the number of viable blastocysts observed as well as qualitative appearance of those blastocysts when observed microscopically.

VI. Assays and Kits

Methods and assay kits with a higher level of sensitivity than standard MEA assays for evaluating embryo impact or toxicity associated with ART products is likewise described herein. The methods can include providing an assay comprising a transgenic embryo having at least the regulatory region of a reporter gene operably linked to a pluripotency marker. Also, a control product which promotes or is known to result in normal embryo development can be provided. The control product can have the same or similar use in ART as the use intended for the test product.

In some embodiments, the product to be tested can be culture media or supplements. As used herein, culture media includes, without limitation, reproductive media and supplements used for assisted reproduction procedures. Media include liquid and powder versions of various substances which come in direct physical contact with embryos (e.g. water, acid solutions used to treat gametes or embryos, rinsing solutions, reagents, sperm separation media, or oil used to cover the media) for the purposes of preparation, maintenance, transfer or storage. Supplements, as used herein, include specific reagents added to media to enhance specific properties of the media such as proteins, sera, antibiotics, or the like.

The acceptability of the test product can be compared to a control product by assessing embryo development at 2-cell-stage, 4-cell stage, 8-cell stage, morula stage, blastocyst stage and/or gastrulation stage. More particularly, the transgenic embryos can be analyzed microscopically to assess differentiation at the blastocyst stage of development. For example, in the case of transgenic murine embryos, the embryos can be assessed at approximately 48 and/or 96 hours after fertilization. In some aspects the methods can include an evaluation at 48 hours, which can be an early predictor of quality of development. For other mammalian embryos, the duration of time from fertilization to blastocyst development can vary depending upon the source of the embryos. For example, blastocyst development for human embryos typically occurs at Day 5. Embryonic viability is assessed based upon assessing or scoring embryo qualitative/quantitative assessment of expression (e.g., via fluorescence), and if desired also with an assessment of morphology.

The acceptable threshold for optimal embryo growth is based on individual set criteria depending on culture conditions and test items. In some aspects, a control benchmark is run in parallel with the test culture medium in each test. For example, when new medium is evaluated for use in an IVF environment, the medium is tested against a control medium which has been pre-determined to provide optimal growth conditions for embryos. New test culture medium is evaluated by assessing blastocyst development relative to the blastocyst development in the control medium. Assessment can include a qualitative comparison of the number of cultured embryos reaching the blastocyst stage in the control medium as compared to the number of embryo reaching the same stage in the test medium. Acceptable quality control generally requires development of at least 80% blastocysts in the test medium in order for a product to pass the test. Additional growth parameters include the number of cells observed at the blastocyst stage in the control versus the test medium as well as the intensity and localization of fluorescence of the reporter gene in the transgenic blastocysts. As compared with the standard MEA assay, where the blastocyst may look normal, the disclosed assay provides a more enhanced sensitivity to embryo development. The reporter gene operably linked to a pluripotency/viability marker (and/or regulatory region thereof) can be observed microscopically and provides a better delineation of gene expression in optimal, sub-optimal, and/or embryo toxic growth conditions. Acceptable limits may be determined, for example, as described in the Analysis of Embryo Development section above.

In some aspects, assessment of the test product does not require comparison to a control product run in parallel. In some aspects, standardized criteria are used to determine whether the test product is acceptable. For example, expression (e.g., via fluorescence analysis) from blastocysts grown under test conditions at various stages may be compared to expression levels that correspond to optimal embryo growth. In some embodiments, the user easily can determine acceptable levels, e.g., based on previous experiments under similar conditions. In some embodiments, the assay includes standards deemed acceptable. In some embodiments, acceptability limits are set by a regulatory agency or similar group. Acceptable limits may be determined, for example, as described in the Analysis of Embryo Development section above.

A quality control assay for use in clinical ART to evaluate products used in the process of handling and preserving human gametes and producing, culturing and preserving human embryos is provided. The assay can include a transgenic one-cell embryo harvested from a transgenic mammal, wherein the transgenic embryo includes at least one reporter gene operably linked to at least one embryonic pluripotency marker. The pluripotency regulator can be a viability marker such as OCT-4, SOX2, Nanog, CDX2 as well as their upstream mediators and downstream effectors that play a role in ensuring normal embryo development. The reporter gene can encode a protein. The protein can include any reporter protein including, without limitation, Green Fluorescent Protein, Red Fluorescent Protein, Cyan Fluorescent Protein, Orange Fluorescent Protein, or Yellow Fluorescent Protein. The assay also includes instructions for evaluating ART products and IVF culture conditions. These instructions include directions relating to incubating a transgenic one-cell embryo under ART conditions and evaluating embryo development based upon morphology and/or gene expression (as determined by reporter gene expression) from the one and two-cell to later blastulation and gastrulation stages. Incubation, as used herein, describes the process by which fertilized, one or two cell embryos are cultured for a predetermined amount of time, e.g. approximately 24-96 hours in a defined culture media.

In one aspect, this invention relates to a quality control assay for use in assessing a media used for Assisted Reproductive Technologies (ART), the assay comprising: one or more transgenic embryos, wherein the embryos comprise at least one reporter gene operably linked to the regulatory region of at least one embryonic viability marker; a control product, wherein the product allows for optimal embryo growth; and instructions for evaluating ART products and IVF culture conditions using the assay. In some embodiments, the control product is control medium. In some embodiments, the assay also includes suboptimal media, wherein the suboptimal media allows for suboptimal embryo growth. In some embodiments, the instructions include standards or guidelines for determining acceptability of the product to be tested for use in ART.

Also disclosed is a molecular MEA kit for use in quality control of clinical human ART/IVF. The kit includes a transgenic one-cell embryo. The transgenic embryo includes at least one reporter gene operably linked to at least the regulatory region of at least one gene associated with embryonic development; and an embryo expressing a transgenic/reporter gene that is differentially expressed under optimal and sub-optimal or embryo-toxic culture conditions. The kit further includes an ART/IVF consumable. An ART consumable can include, without limitation, embryo culture media, gamete handling media, enzymes for denuding oocytes, gradient for sperm separation, freezing media, thawing media, pipettes and embryo handling devices, labware used in the process of human in vitro fertilization including but not limited to Petri dishes, centrifuge tubes, cryopreservation and cryostorage devices.

EXAMPLES

Additional embodiments are disclosed in further detail in the following examples, which are not in any way intended to limit the scope of the claims.

Example 1: Evaluation of Puripotency Regulators

Several factors such as toxicity and sterility of the culture media or materials used in ART can affect development of embryos. The following examples describe assays to assess embryonic viability under optimal and sub-optimal culture conditions. Embryos in which pluripotency regulators were visualized using a fluorescent microscope are shown. The pluripotency markers used for assessing embryonic development from one or two cell stage of development include, for example, SOX2, Oct-4, Nanog as well as their upstream mediators and downstream effectors that play a role in ensuring normal embryo development.

To test culture media, media additives, or ART consumables, the collected transgenic embryos are first incubated in 50 µL droplets of either control medium (medium which has already been determined to promote optimal blastocyst development) or test media. In each case the embryos are covered by mineral oil and incubated at 37 degrees C. under classical cell culture conditions (humidified atmosphere of 5% CO2 in air). On day 1, 2, and/or 3, embryos are selected for assays and transferred in the medium to be tested. The embryos are cultivated until day 5. By comparing the rates of blastocysts stages reached versus control groups, a cytotoxic or sub-optimal effect can be identified which interferes with embryo development.

a. Expression of OCT-4 in Mouse Embryo

FIG. 1 is a photograph from the fluorescence microscope showing expression of the pluripotency regulator OCT-4 in early-stage mouse embryos. The 2-cell embryo was cultured in vitro in optimal (control) and suboptimal (test) conditions. After approximately 48 hours, the embryos were stained with an antibody specific for OCT-4 (red) and evaluated via fluorescence microscopy. (OCT-4 is also called OCT-3/4.) As is evident from FIG. 1, the embryo on the left, which was incubated under optimal growth conditions, is well developed with uniform staining By contrast, the blastocyst on the right was incubated in sub-optimal growth conditions. A lack of OCT-4 staining is observed on the right cell of the embryo on the right, demonstrating that the sub-optimal growth conditions result in slower embryonic development and reduced OCT-4 expression, even at an early stage of embryo development.

b. Expression of OCT-4 in Mouse Blastocyst

FIGS. 2A and 2B illustrate expression of OCT-4 at the blastocyst stage. The embryos were cultured in vitro for 96 hours, then stained with DAPI (blue nuclear stain, left image) and an anti-OCT-4 antibody (red, center image) and observed via a fluorescence microscope. The right image in each Figure represents a merged image of the DAPI and OCT-4 images; overlap of staining is indicated in purple. In FIG. 2A, under optimal growth conditions, normal embryo development is observed as demonstrated by the uniform OCT-4 staining. By contrast, in FIG. 2B, the embryos were incubated under sub-optimal growth conditions. A lack of OCT-4 staining on some mural trophectoderm cells is observed in the embryos, as noted by the arrows on FIG. 2B. Without the use of the presently claimed technology, the sub-optimal culture conditions would not be evident or identifiable as sub-optimal when using the conventional MEA standard QC protocol of morphological assessment because the blastocyst appears to be normal and developing at a normal rate. However, by observing the slow growth in FIG. 2B, it is clear that blastocyst development is qualitatively less uniform and less optimal than in the embryonic development and blastocyst differentiation observed in FIG. 2A.

c. Expression of Sox2 in Mouse Blastocyst

Figure 3A:
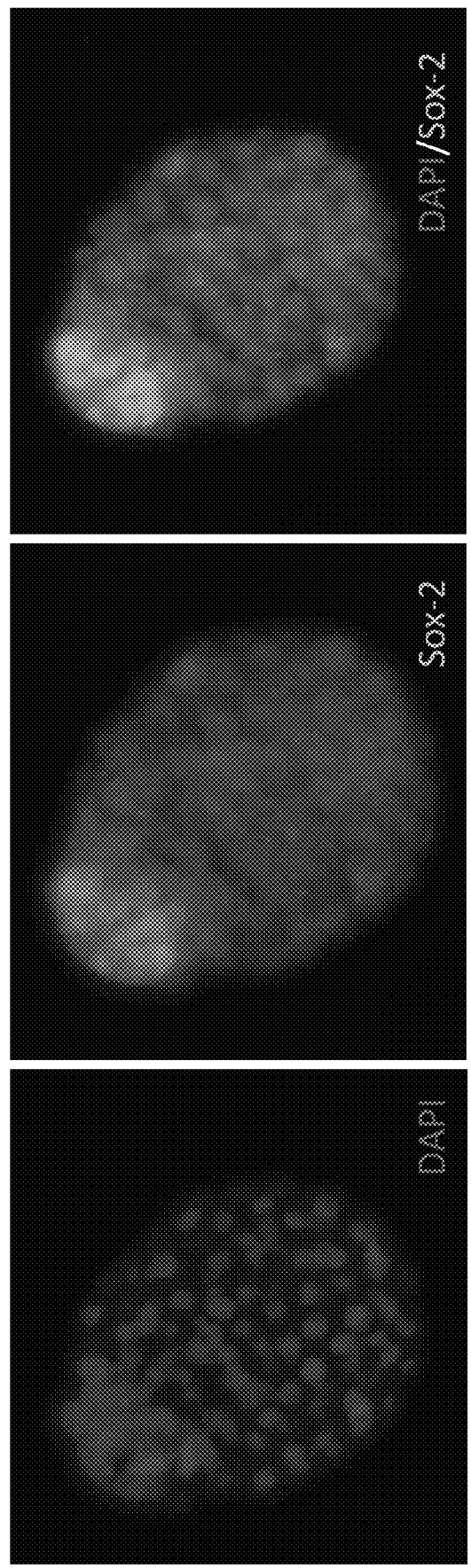
Figure 3B:
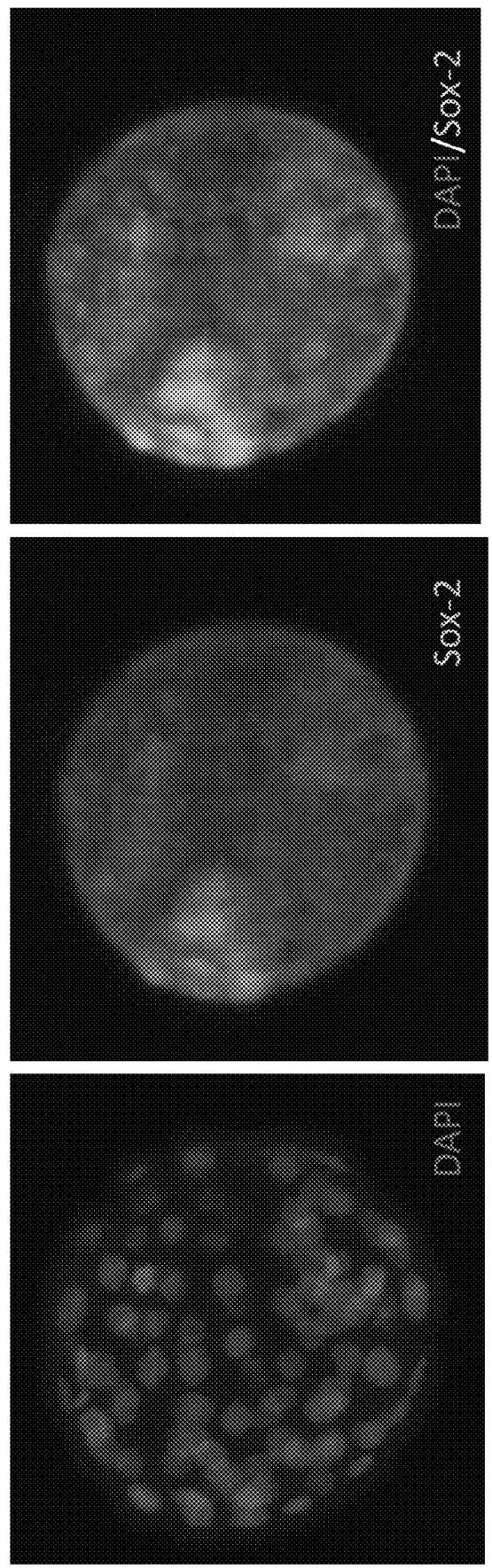

FIGS. 3A, 3B, and 3C demonstrate the expression pattern of Sox2 in embryos grown under optimal or suboptimal conditions. FIGS. 3A-3C are fluorescence microscopy photographs of control murine embryos. Embryos were incubated to the blastocyst stage in vitro, fixed, stained with DAPI (blue) and anti-Sox2 antibody (green), and observed microscopically. After 96 hours of culture, the image on the left of FIG. 3A shows DAPI staining of the embryo. The center image in FIG. 3A shows the staining pattern for the Sox2 viability marker, and the image on the right is a merged image. The staining pattern observed in the embryo is uniform and evidences normal, healthy blastocyst development under optimal conditions. Notice the uniform staining as well as the well-defined differentiation of the blastocyst.

Turning to FIG. 3B, blastocysts incubated in sub-optimal growth conditions are observed. After 96 hours, the embryo was fixed and stained with DAPI (blue) and anti-Sox2 antibody (green), and observed microscopically to assess growth. The picture appears to demonstrate normal growth and development despite the sub-optimal culture conditions.

FIG. 3C shows two embryos stained with DAPI (blue) and anti-Sox2 antibody (green) with poor growth in suboptimal culture conditions.

d. Expression of CDX-2 in Mouse Blastocyst

Figure 4:
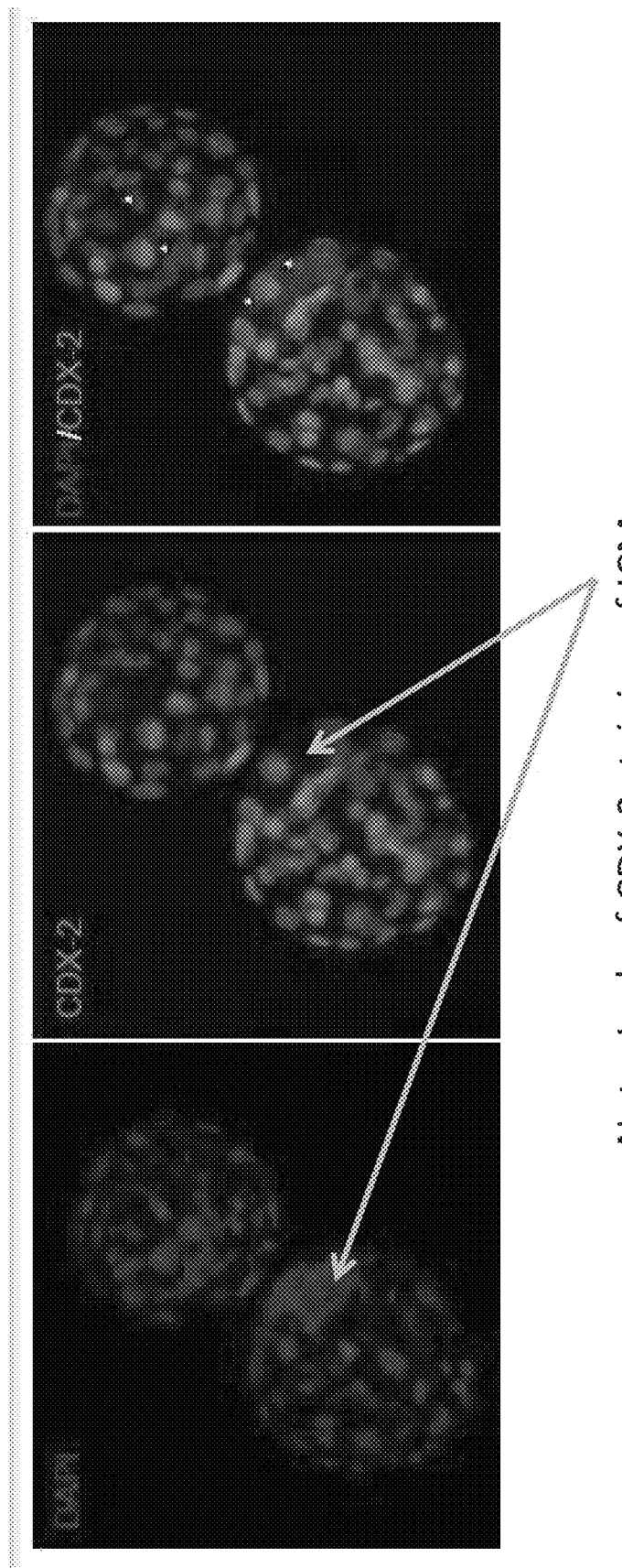
FIG. 4 is a color photograph of mouse embryos incubated under optimal growth conditions to the blastocyst stage. The embryos were stained with DAPI (blue) and anti-CDX-2 antibody (green), then photographed under fluorescence microscopy.

FIG. 4 further demonstrates the superior assessment or quality control capability features of the technology. FIG. 4 represents fluorescence microscopy photographs of control murine embryos. Embryos were incubated to the blastocyst stage in vitro, stained, and observed microscopically. After 96 hours of culture, the image on the left of FIG. 4 shows an embryo that was fixed and stained with DAPI (blue) and observed microscopically to assess growth. The staining pattern observed in the embryo is uniform and evidences normal, healthy blastocyst development under optimal conditions. The center image in FIG. 4 shows the embryo having the CDX-2 transcription factor stained with green fluorescence. The image on the right in FIG. 4 is a merged image of CDX-2 and DAPI staining Notice the uniform staining of the trophectoderm, but not the inner cell mass. Arrows show non-stained inner cell mass.

Example 2: Molecular Mouse Embryonic Assay

Transgenic mice containing a reporter gene linked to pluripotency marker(s) were used to carry out molecular-based mouse embryo assay (mMEA) under optimal and sub-optimal conditions. Transgenic male mice (B6;CBA-Tg (Pou5f1-EGFP)2Mnn/J; Jackson Laboratory) expressing enhanced green fluorescent protein (EGFP) under the control of the POU protein domain, class 5, transcription factor 1 (Pou5f1, a.k.a. Oct-4) promoter and distal enhancer were used.

Transgenic male mice were mated with super-ovulated wild type (B6D2F1) female mice. One-cell embryos were collected and cultured in groups of 3 to 4 embryos per 20 µL drop of medium, or a single embryo per 10 µL drop of medium, depending on experiment performed. Embryos were cultured for 96 hours under optimal or sub-optimal conditions. Fluorescence indicates expression of the Oct-4-EGFP transgene.

a. Comparison of Morphological Development and Oct-4 Expression During Embryo Development One-cell embryos were cultured in groups of 3 to 4 embryos per 20 µL drop of medium under optimal and suboptimal conditions. Embryo development was assessed after 48 hours of culture using both light (stereoscope) and UV (inverted microscope with UV light) microscopy to check embryo morphology, determine developmental stage and evaluate levels of Oct-4 expression as a function of the fluorescence intensity of GFP. The same embryos were assessed by both methods. Embryo development as determined by light microscopy (FIG. 5A) showed both 8-cell and <8-cell embryos, and fluorescence intensity (FIG. 5B) was characterized as low (no light to low light, 0-1) or high (medium to high light, 2-3). As shown in FIG. 5B, 8-cell embryos with normal morphology may have low expression of Oct-4 as demonstrated by the low intensity (arrow) of the 8-cell embryo.

b. Correlation of Fluorescence Pattern/Intensity with Embryo Development—Analysis of Multiple Embryos One-cell embryos were collected and cultured in groups of 3 to 4 embryos per 20 µL drop of medium under optimal or suboptimal conditions. Blinded assessment of each group of embryos was performed at 48 hours by two evaluators: one evaluator determined the morphology of the group of embryos by light microscopy (stereoscope); the second evaluator determined the fluorescence intensity of the group of embryos. Another assessment of each group of embryos was done at 96 hours to determine blastocyst development.

Figure 6B:
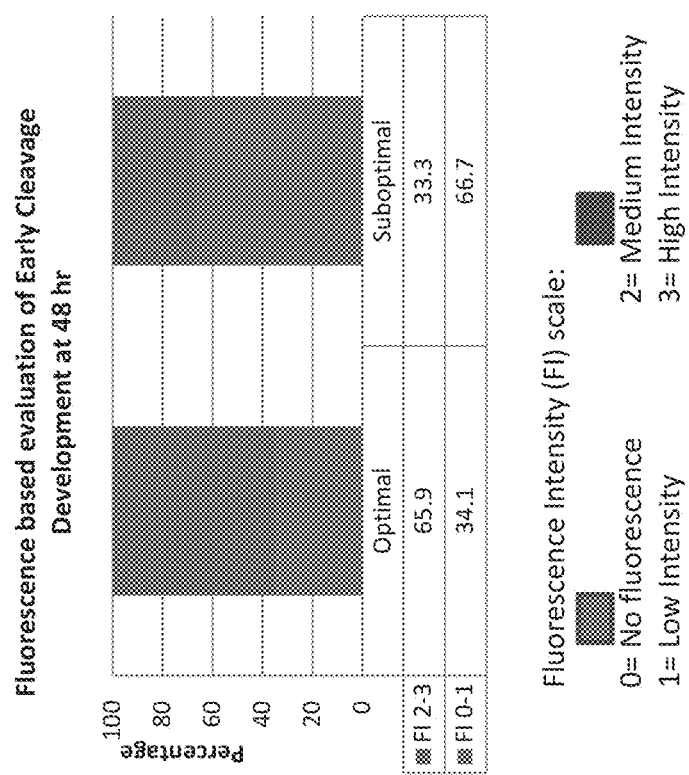
FIGS. 6A-6E indicate the correlation between early fluorescence and blastocyst development in transgenic mouse embryos expressing EGFP under the control of the Oct-4 promoter and distal enhancer that were cultured under optimal or suboptimal conditions. Each embryo was examined under light and fluorescence microscopy after 48 and 96 hours.
Figure 6A:
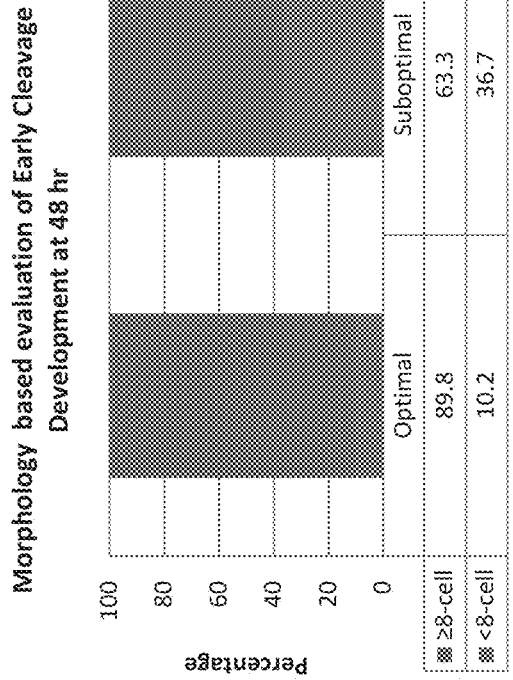
Figure 6D:
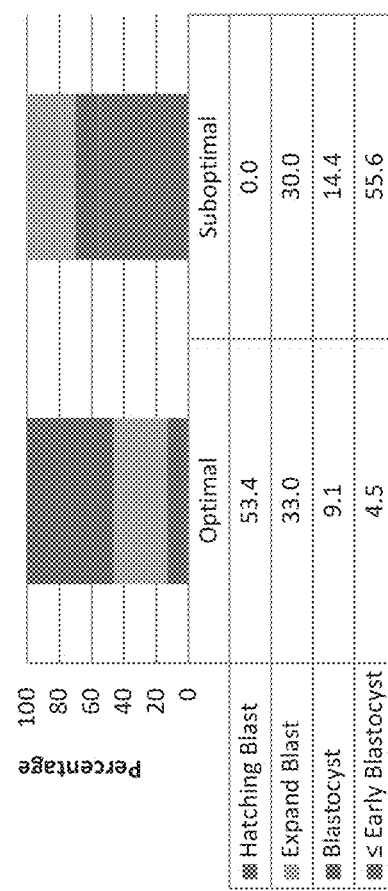
Figure 6C:
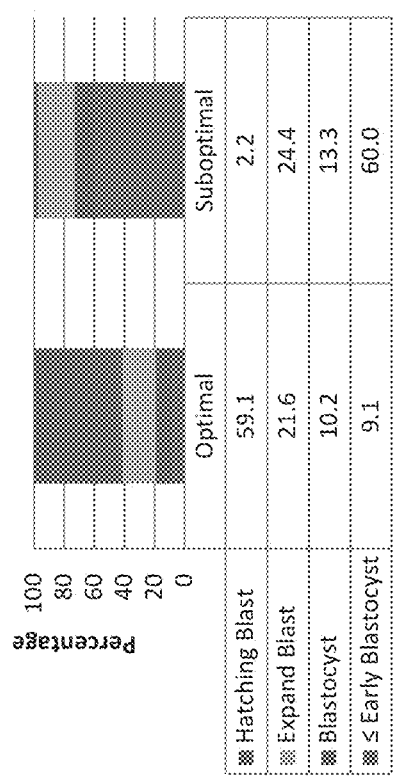
Figure 6E:
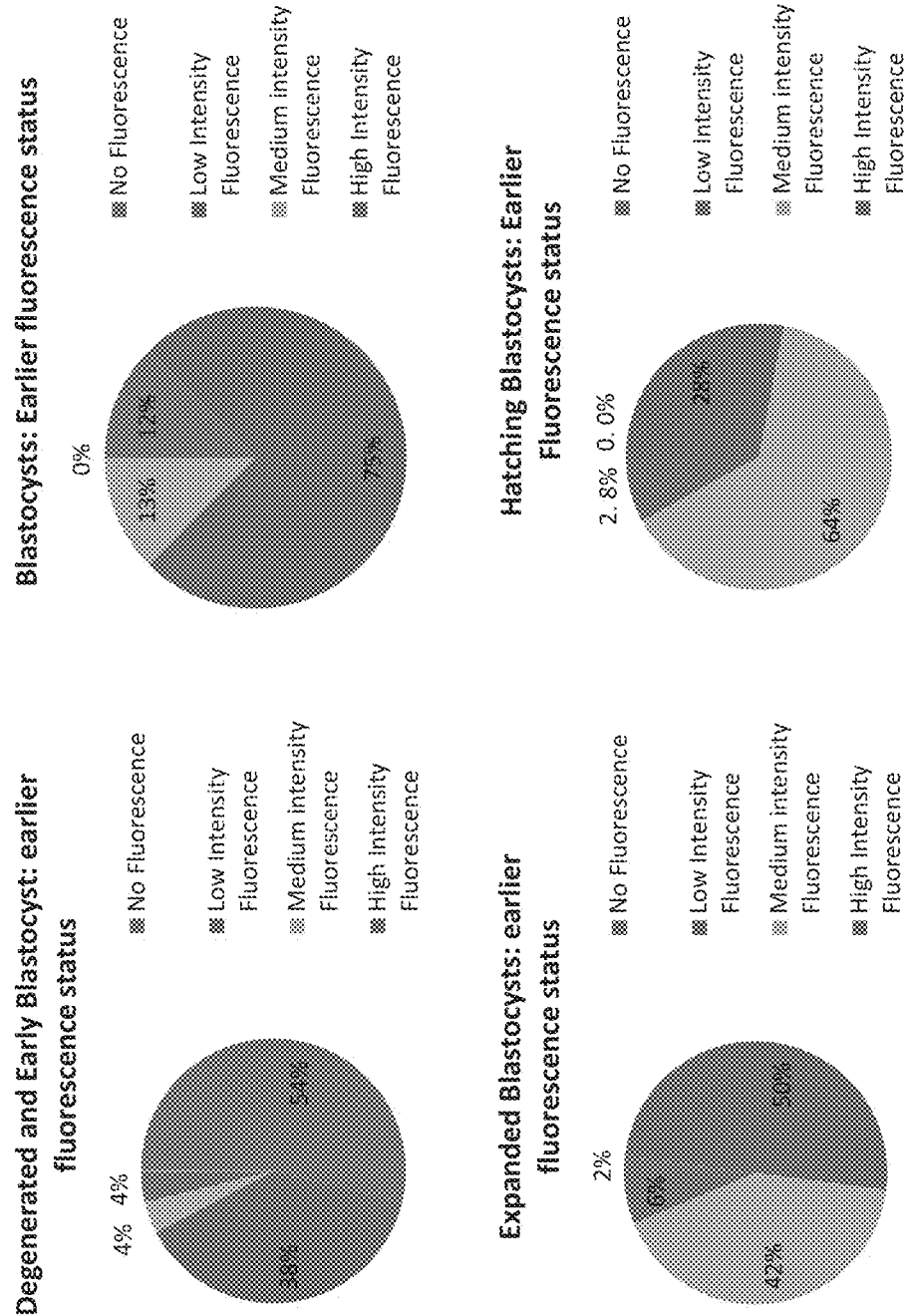

FIG. 6A indicates the percentage of groups of embryos with 8 cells or more (red: ≥8-cell) or less than 8 cells (blue: <8-cell) at 48 hours by morphology analysis by light microscopy. FIG. 6B indicates the percentage of embryos with the indicated fluorescence intensity (blue: fluorescence 0-1; red: fluorescence 2-3) at 48 hours. 0=No fluorescence; 1=low intensity; 2=medium intensity; 3=high intensity. Comparison of the two methods at 48 hours for the suboptimal condition showed that the morphology-based assay determined that 63.3% of the embryos had progressed to the 8-cell stage or beyond, in contrast to the fluorescence-based assay which determined that only 33.3% of the embryos had the desired (medium to hi) fluorescence intensity. The molecular MEA was more sensitive than the standard MEA at an earlier stage for determining that the growth conditions were suboptimal. FIGS. 6C and 6D indicate the blastocyst development as determined by light microscopy (FIG. 6C) and fluorescent microscopy (FIG. 6D) at 96 hours (blue: early blastocyst; red: blastocyst; green: expanded blastocyst; purple: hatching blastocyst) was no different. FIG. 6E indicates the correlation of fluorescence intensity at 48 hours with the blastocyst stage of the same embryo at 96 hours, as a percentage of blastocysts at a given stage that exhibited the indicated fluorescence at 48 hours (blue: no fluorescence; red: low intensity fluorescence; green: medium intensity fluorescence; purple: high intensity fluorescence). Good correlation was observed between early expression of OCT-4 (fluorescence) and progression to later stages of embryo development for individual embryos. FIG. 7 indicates the distribution of embryos in optimal (blue line) and suboptimal (red line) culture conditions according to their fluorescence status, shown as the percent of embryos exhibiting each fluorescence intensity at 48 hours.

Example 3: Molecular Mouse Embryonic Assay Used to Assess Blastocyst Development in Presence of Different Qualities of Oil Transgenic mouse embryos containing CDX2-GFP were used to carry out molecular-based mouse embryo assay (mMEA) in the presence of different qualities of oil: (1) good oil, (2) 5% bad oil, (3) 7.5% bad oil, (4) 10% bad oil, and (5) 15% bad oil. Eighteen embryos were tested for each of the above-listed oil qualities. The embryos were evaluated using a stereo microscope to at 48 and 96 hours to assess morphologically blastocyst development, and also using a fluorescent microscope at 48 and 96 hours to assess expression of GFP. Using conventional MEA protocols, any embryo scoring at or above 80% at 96 hr (expanded and hatching blastocysts) would pass such that the tested parameter would be deemed accessible. As shown below, the morphological analysis alone was not as sensitive as the molecular expression methodology and would have resulted in one false positive for the 7.5% bad oil.

a. Morphological Evaluation of Development and Cdx-2 Expression at 48 Hours

Figure 8A:
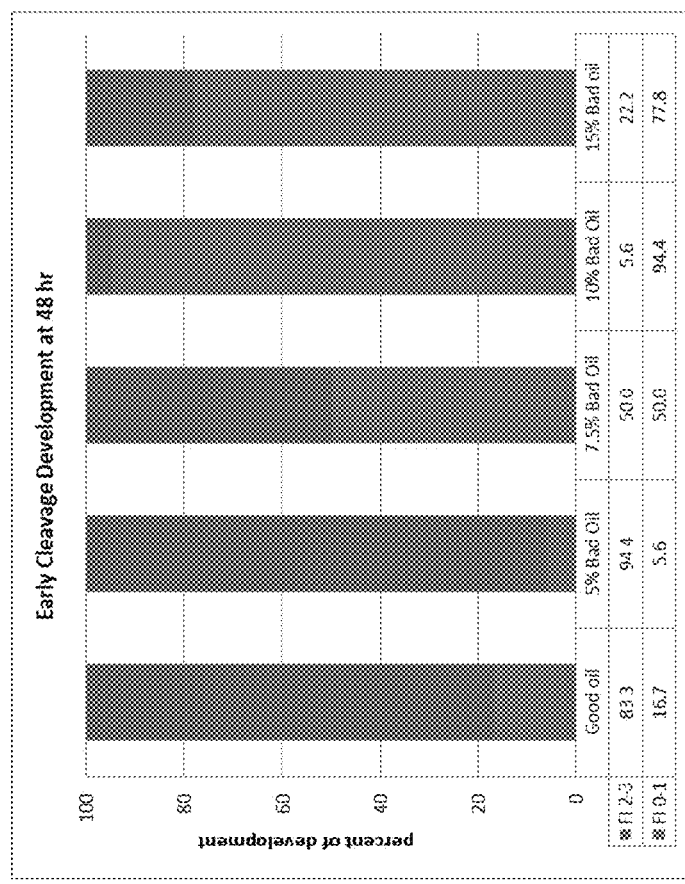
Figure 8B:
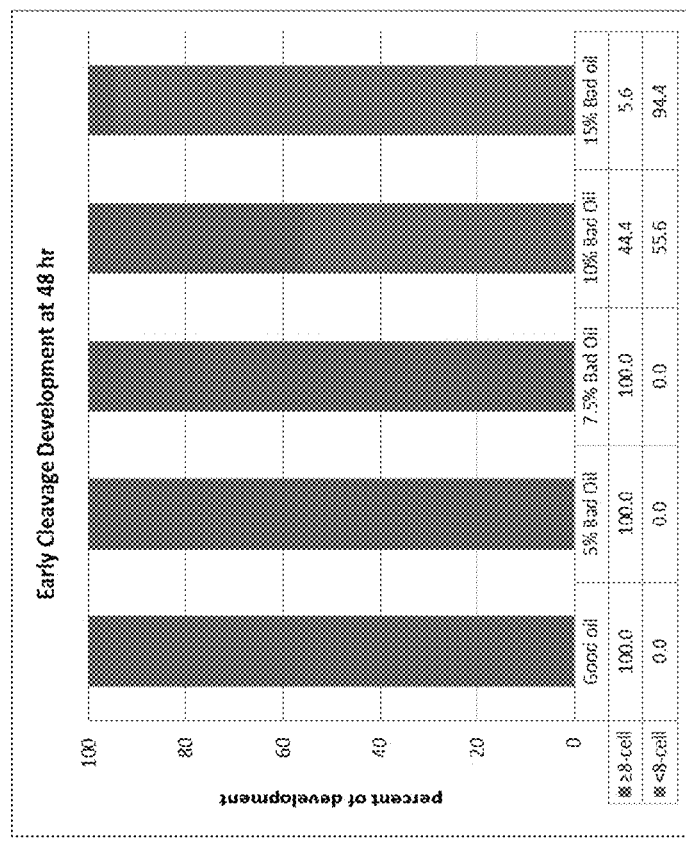

FIG. 8A shows the early cleavage development of embryos for morphology assessment after 48 hours, specifically the percentage of embryos with less than 8 cells (blue) and those with greater than or equal to 8 cells (red). The Cdx-2 expression/fluorescence intensity of the same embryos was also evaluated at 48 hr. Embryos were rated on a relative subjective scale of 0-3 for fluorescence with 0 meaning no fluorescence, 1 meaning low fluorescence, 2 meaning medium fluorescence, and 3 meaning high fluorescence. The percent of developing embryos rated as 0-1 (no or low fluorescence, blue) 2-3 (medium or high fluorescence, red) are shown in FIG. 8B.

b. Morphological Evaluation of Development and Cdx-2 Expression at 96 Hours

Figure 8C:
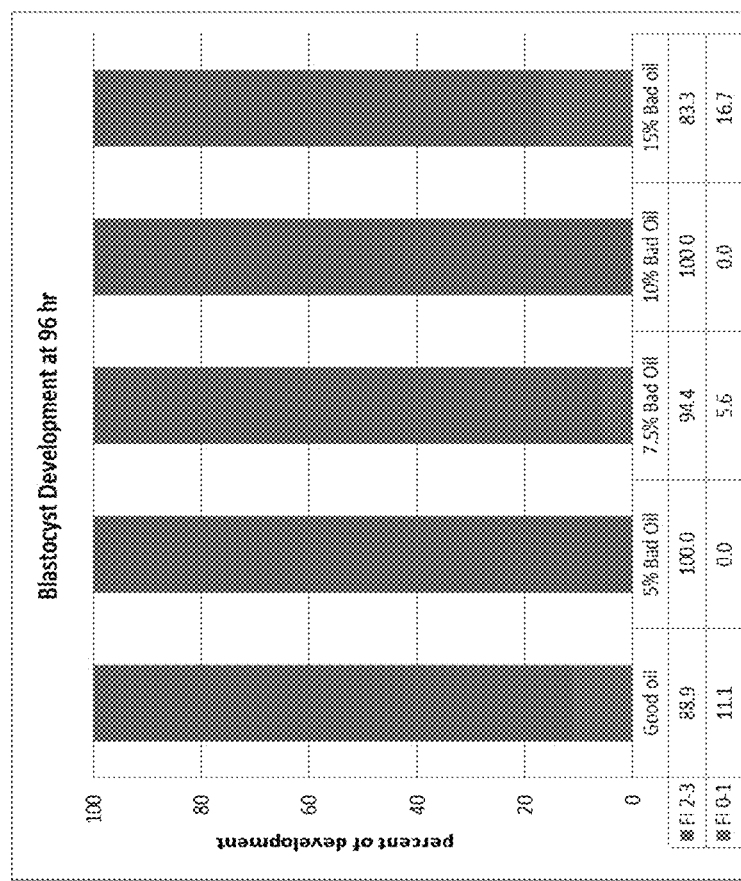
Figure 8D:
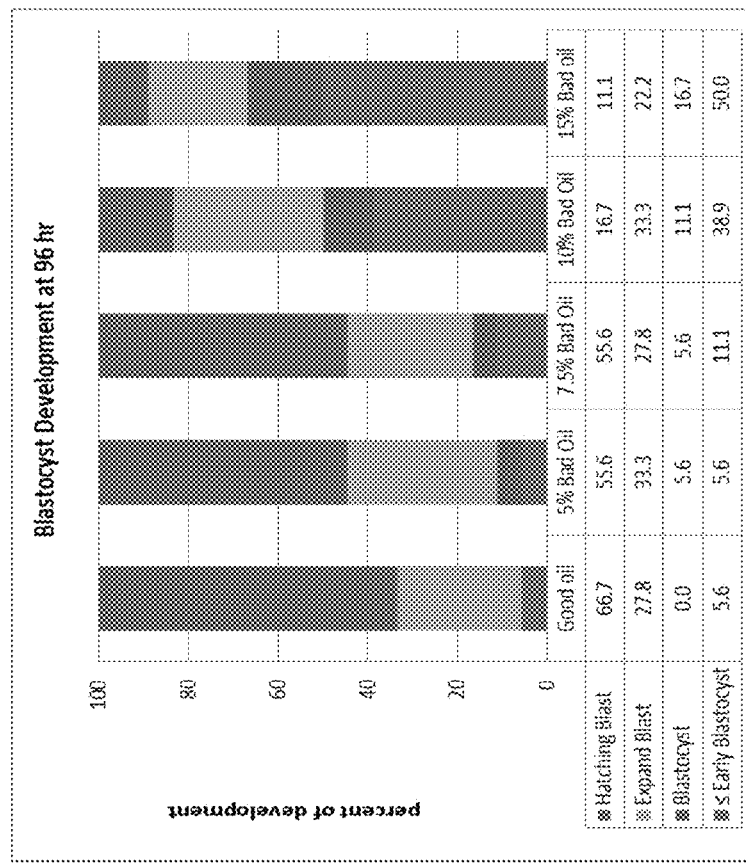

FIGS. 8C and 8D indicate the blastocyst development as determined by light microscopy (FIG. 8C) and fluorescent microscopy (FIG. 8D) at 96 hours (blue: early blastocyst; red: blastocyst; green: expanded blastocyst; purple: hatching blastocyst). As shown in FIG. 8C, the "good oil," the "5% bad oil," and the "7.5% bad oil" all meet the 80% threshold using MEA or morphological analysis for being deemed acceptable. The 10% and 15% bad oils would have failed the 80% threshold. Evaluation of blastocysts specifically for fluorescence intensity at 96 hr does not distinguish the development differences between optimal and suboptimal conditions. FIG. 8E indicates the distribution of embryos in the various treatment conditions according to their fluorescence status, shown as the number of embryos exhibiting each fluorescence intensity at 48 hours. Embryos were rated on a relative subjective scale of 0-3 for fluorescence with 0 meaning no fluorescence, 1 meaning low fluorescence, 2 meaning medium fluorescence, and 3 meaning high fluorescence.

e. Discussion/Summary of Results

Tables 1 and 2 below show that using only the morphological assessment would have led to a false positive for the 7.5% bad oil*. In contrast, the molecular MEA identified the suboptimal development as early as 48 hours. As illustrated by the data in Table 2, using morphology alone, the 7.5% bad oil would have scored above the 80% cutoff, while the developmental expression of Cdx-2 demonstrated that those embryos were adversely affected by the 7.5% bad oil. This illustrates the increased sensitivity according to some embodiments provided by the molecular MEA as described herein as compared to only visual morphological analysis.

TABLE 1

% of early cleavage development at 48 hours

|  | Morphology ≥8-cell | Fluorescence FI 2-3 |
|---|---|---|
| Good oil (control) | 100.0 | 83.3 |
| 5% Bad Oil | 100.0 | 94.4 |
| 7.5% Bad Oil* | 100.0 | 50.0 |
| 10% Bad Oil | 44.4 | 5.6 |
| 15% Bad oil | 5.6 | 22.2 |

TABLE 2

% of blastocyst stage development at 96 hours

|  | Morphology/Expected Hatching |
|---|---|
| Good oil | 94.4 |
| 5% Bad Oil | 88.9 |
| 7.5% Bad Oil | 83.3 |
| 10% Bad Oil | 50.0 |
| 15% Bad oil | 33.3 |

Example 4: Molecular Mouse Embryo Assay Case Study a. Determination of Suboptimal Media Components Transgenic mouse embryos containing a reporter gene linked to pluripotency marker were incubated in 20 µL droplets of medium containing human serum albumin (HSA) of differing quality. The embryos were covered by mineral oil and incubated at 37 degrees C. under classical cell culture conditions (humidified atmosphere of 5% CO2 in air). Embryos were evaluated morphologically and for expression of GFP after 48 and 96 hours in culture.

At 48 h, the embryos were assessed by standard MEA and molecular MEA. The results are shown in Table 3. All of the HSA samples gave similar results with the standard MEA (top panel), with 95.3% to 97.7% of the embryos progressing to the 8-cell stage or beyond in each condition. The molecular MEA (lower panel) identified two HSA samples (HSA-A and HSA-D) that exhibited a greater number of embryos with no to low fluorescence.

TABLE 3

|  | below 4-cell | 4 to 7-cell | ≥8-cell |
|---|---|---|---|
| HSA-A | 0.0 | 4.5 | 95.5 |
| HSA-B | 0.0 | 4.7 | 95.3 |
| HSA-C | 0.0 | 2.3 | 97.7 |
| HSA-D | 0.0 | 2.3 | 97.7 |
| HSA-F | 0.0 | 4.7 | 95.3 |

|  | No Fluorescence | Low Fluorescence | Med to Hi fluorescence |
|---|---|---|---|
| HSA-A | 0.0 | 13.6 | 86.4 |
| HSA-B | 0.0 | 9.3 | 90.7 |
| HSA-C | 2.3 | 4.7 | 93.0 |
| HSA-D | 2.3 | 16.3 | 81.4 |
| HSA-F | 0.0 | 4.7 | 95.3 |

At 96 h, the embryos were assessed to determine the percentage of embryos in each stage. The results are shown in Table 4. HSA-B, HSA-C, and HSA-F allowed greater than 85% of the embryos to progress to the expanded blastocyst stage and beyond, which surpasses the requirements for allowable IVF culture media. HSA-D allowed 83.7% of the embryos to progress to the expanded blastocyst stage and beyond, which barely passes the requirements for allowable IVF culture media. HSA-A allowed only 72.7% of the embryos to progress to the expanded blastocyst stage and beyond, which fails the requirements for allowable IVF culture media. The molecular MEA identified the suboptimal culture conditions at an earlier stage (48 h) than the standard MEA.

TABLE 4

| | ≤Early Blastocyst | Blastocyst | Expand Blast | Hatching/ hatched | Exp + Hatch |
|---|---|---|---|---|---|
| HSA-A | 11.4 | 15.9 | 25.0 | 47.7 | 72.7 |
| HSA-B | 4.7 | 9.3 | 20.9 | 65.1 | 86.0 |
| HSA-C | 4.7 | 2.3 | 11.6 | 81.4 | 93.0 |
| HSA-D | 0.0 | 16.3 | 16.3 | 67.4 | 83.7 |
| HSA-F | 0.0 | 4.7 | 16.3 | 79.1 | 95.3 |

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

What is claimed is:

1. A method for assessing a product or culture condition for use in human Assisted Reproductive Technologies (ART), the method comprising:
   (i) microscopically evaluating the fluorescence intensity or light emission of at least one fluorescent reporter gene operably linked to a regulatory region of OCT-4 during at least one stage of development of a transgenic murine test embryo,
   wherein the test embryo comprises at least one cell and has been cultured in vitro in contact with the product or culture condition for a specified duration, and wherein the stage is a developmental stage between 1-cell zygote through blastocyst; and
   (ii) determining the acceptability of the product or culture condition for use in human ART based upon the evaluation, wherein the product or culture condition is deemed acceptable when the fluorescence intensity or light emission of the fluorescent reporter gene in the test embryo is greater than a threshold level of the fluorescence intensity or light emission and/or localization of fluorescence of a reporter gene in a control embryo.

2. The method of claim 1, further comprising evaluating the morphology of the embryo during at least one stage of development of said embryo.

3. The method of claim 1, wherein the transgenic embryo is a one-cell embryo or a two-cell embryo.

4. The method of claim 1, wherein the at least one fluorescent reporter gene encodes a fluorescent protein selected from the group consisting of green fluorescent protein, red fluorescent protein, cyan fluorescent protein, orange fluorescent protein, yellow fluorescent protein.

5. The method of claim 1, wherein said evaluating step comprises:
   (i) capturing at least one image of said embryo;
   (ii) determining at least one of fluorescence intensity or light emission and/or localization of fluorescence of said reporter gene based on the image.

6. The method of claim 5, wherein step (ii) is performed by a computer.

7. The method of claim 1, wherein the control embryo has been cultured in the absence of the product or culture condition.

8. The method of claim 1, wherein the at least one stage of development is 1-cell stage, 2-cell stage, 4-cell stage, 8-cell stage, morula stage, and/or blastocyst stage.

9. The method of claim 1, wherein the product is selected from the group consisting of needles, catheters, microtools, labware, syringes, tissue culture dishes, tissue culture plates, pipette tips, dishes, plates, water, water purification systems, gamete and embryo culture media, gamete and embryo handling/processing media, transport media, enzymes for denuding oocytes, gradient for sperm separation, freezing/vitrification media, thawing/warming media, pipette and embryo handling devices, lab-ware used in the process of human ART including but not limited to Petri dishes, centrifuge tubes, cryopreservation and cryo-storage devices, and any solutions, reagents or devices involved with ART, media supplements, and other vessels, devices, or reagents that come into physical contact with gametes, embryos or tissue culture media.

10. The method of claim 1, wherein the control embryo has been cultured with a control product.

11. The method of claim 1, wherein the fluorescence intensity or light emission of the fluorescent reporter gene is greater than a threshold level in a given location of the cell to indicate that the test embryo is not affected by use of the product or culture condition when the reporter gene is expressed at or above a threshold level and in the location.

12. The method of claim 11, wherein the fluorescent reporter gene is normally expressed in the cytoplasm at a time when fluorescence intensity or light emission is evaluated, and the conditions are deemed optimal when the fluorescence intensity or light emission in the cytoplasm of the test embryo is higher than the threshold level of the fluorescence intensity or light emission in the cytoplasm of the control embryo.

13. The method of claim 11, wherein the fluorescent reporter gene is normally expressed in the nucleus at a time when fluorescence is evaluated, and the conditions are deemed optimal when the fluorescence in the nucleus of the test embryo is higher than the threshold level of fluorescence in the nucleus of the control embryo.

14. The method of claim 1, wherein the threshold level comprises at least one of 50% or greater, 60% or greater, 70% or greater, 80% or greater, 90% or greater, or 100% or greater of the fluorescence intensity or the light emission of a reporter gene observed in a given location of the control embryo.

15. The method of claim 14, wherein a plurality of test embryos are cultured and the conditions are deemed suboptimal when the fluorescence from less than 80% of the test embryos is equal to or greater than the threshold level of at least one of 50% or greater, 60% or greater, 70% or greater, 80% or greater, 90% or greater, or 100% or greater fluorescence intensity or light emission from the control embryo.

16. The method of claim 15, wherein suboptimal culture conditions indicate that the product is not suitable for use in human ART.

17. The method of claim 1, wherein fluorescence intensity is ranked on a scale wherein a score of 0 indicates no fluorescence intensity, a score of 1 indicates low fluorescence intensity, a score of 2 indicates medium fluorescence intensity, and a score of 3 indicates high fluorescence intensity.

18. The method of claim 17, comprising culturing a plurality of test embryos under the specified conditions, wherein the conditions are deemed suboptimal when less than 60% of the test embryos exhibit fluorescence at a medium to high level.

19. The method of claim 17, wherein acceptability of the product or culture condition is dependent on from about 60% to about 100% of the test embryos exhibiting fluorescence intensity at or above the fluorescence intensity of the control embryos, wherein the control embryos have a score of 2 or above.

* * * * *